United States Patent
Ostrovsky et al.

(10) Patent No.: US 9,345,472 B2
(45) Date of Patent: May 24, 2016

(54) MULTI-ARM TOOL FOR DELIVERING IMPLANTS AND METHODS THEREOF

(75) Inventors: Isaac Ostrovsky, Wellesley, MA (US); Jozef Slanda, Milford, MA (US); Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 258 days.

(21) Appl. No.: 13/598,143

(22) Filed: Aug. 29, 2012

(65) Prior Publication Data
US 2013/0060261 A1  Mar. 7, 2013

Related U.S. Application Data

(60) Provisional application No. 61/530,511, filed on Sep. 2, 2011.

(51) Int. Cl.
*A61F 2/00* (2006.01)
*A61F 2/02* (2006.01)
*A61B 17/04* (2006.01)
*A61B 17/062* (2006.01)
*A61B 17/00* (2006.01)

(52) U.S. Cl.
CPC ......... *A61B 17/0469* (2013.01); *A61B 17/0483* (2013.01); *A61B 17/0485* (2013.01); *A61B 17/0625* (2013.01); *A61B 2017/00349* (2013.01); *A61B 2017/00805* (2013.01)

(58) Field of Classification Search
CPC ........... A61B 17/0469; A61B 17/0483; A61B 2017/00805; A61B 17/0625; A61B 2017/00349; A61B 17/0485; A61F 2/0036; A61F 2/005; A61F 2/0009; A61F 2/04; A61F 6/08; A61F 2250/0007; A61F 2250/0031; A61F 2002/047; A61F 2/004
USPC ......... 606/139; 600/37, 29–32; 128/897–899, 128/834, 885
See application file for complete search history.

(56) References Cited

U.S. PATENT DOCUMENTS

| | | | |
|---|---|---|---|
| 3,946,740 | A | 3/1976 | Bassett |
| 4,373,530 | A | 2/1983 | Kilejian |
| 4,541,427 | A | 9/1985 | Koss |

(Continued)

FOREIGN PATENT DOCUMENTS

| | | |
|---|---|---|
| EP | 0315371 A2 | 5/1989 |
| EP | 2033583 A1 | 3/2009 |

(Continued)

OTHER PUBLICATIONS

Search Report and Written Opinion for International Application No. PCT/US2012/053105, mailed Dec. 11, 2012, 22 pages.

(Continued)

*Primary Examiner* — Navin Natnithithadha
*Assistant Examiner* — Sunita Reddy
(74) *Attorney, Agent, or Firm* — Brake Hughes Bellermann LLP

(57) ABSTRACT

In a general aspect, a medical device includes a receiving arm configured to be coupled to at least a portion of an implant, and a clamping arm having a proximal end coupled to the receiving arm and having a track at a distal end of the clamping arm. The medical device also includes a sliding component including a needle and configured to slidably move along the track of the clamping arm.

19 Claims, 23 Drawing Sheets

(56) References Cited

U.S. PATENT DOCUMENTS

| | | | |
|---|---|---|---|
| 4,923,461 A | 5/1990 | Caspari et al. |
| 5,337,736 A | 8/1994 | Reddy |
| 5,362,294 A | 11/1994 | Seitzinger |
| 5,364,408 A | 11/1994 | Gordon |
| 5,383,904 A | 1/1995 | Totakura et al. |
| 5,507,754 A | 4/1996 | Green et al. |
| 5,549,617 A | 8/1996 | Green et al. |
| 5,562,689 A | 10/1996 | Green et al. |
| 5,603,718 A | 2/1997 | Xu |
| 5,611,515 A | 3/1997 | Benderev et al. |
| 5,628,757 A | 5/1997 | Hasson |
| 5,667,488 A | 9/1997 | Lundquist et al. |
| 5,817,074 A | 10/1998 | Racz |
| 5,840,011 A | 11/1998 | Landgrebe et al. |
| 5,899,909 A | 5/1999 | Claren et al. |
| 5,928,244 A | 7/1999 | Tovey et al. |
| 5,928,252 A | 7/1999 | Steadman et al. |
| 5,934,283 A | 8/1999 | Willem et al. |
| 5,964,732 A | 10/1999 | Willard |
| 6,010,447 A | 1/2000 | Kardjian |
| 6,042,534 A | 3/2000 | Gellman et al. |
| 6,042,536 A | 3/2000 | Tihon et al. |
| 6,056,688 A | 5/2000 | Benderev et al. |
| 6,074,395 A | 6/2000 | Trott et al. |
| 6,110,101 A | 8/2000 | Tihon et al. |
| 6,117,067 A | 9/2000 | Gil-Vernet |
| 6,221,005 B1 | 4/2001 | Bruckner et al. |
| 6,245,082 B1 | 6/2001 | Gellman et al. |
| 6,264,676 B1 | 7/2001 | Gellman et al. |
| 6,273,852 B1 | 8/2001 | Lehe et al. |
| 6,306,079 B1 | 10/2001 | Trabucco |
| 6,328,686 B1 | 12/2001 | Kovac |
| 6,368,859 B1 | 4/2002 | Atala |
| 6,382,214 B1 | 5/2002 | Raz et al. |
| RE37,815 E | 8/2002 | Rizvi |
| 6,475,139 B1 | 11/2002 | Miller |
| 6,502,578 B2 | 1/2003 | Raz et al. |
| 6,506,190 B1 | 1/2003 | Walshe |
| 6,533,795 B1 | 3/2003 | Tran et al. |
| 6,575,897 B1 | 6/2003 | Ory et al. |
| 6,575,998 B2 | 6/2003 | Beyar |
| 6,595,911 B2 | 7/2003 | LoVuolo |
| 6,596,001 B2 | 7/2003 | Stormby et al. |
| 6,596,011 B2 | 7/2003 | Johnson et al. |
| 6,612,977 B2 | 9/2003 | Staskin et al. |
| 6,638,210 B2 | 10/2003 | Berger |
| 6,638,211 B2 | 10/2003 | Suslian et al. |
| 6,641,524 B2 | 11/2003 | Kovac |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,666,817 B2 | 12/2003 | Li |
| 6,673,010 B2 | 1/2004 | Skiba et al. |
| 6,689,047 B2 | 2/2004 | Gellman |
| 6,691,711 B2 | 2/2004 | Raz et al. |
| 6,752,814 B2 | 6/2004 | Gellman et al. |
| 6,755,781 B2 | 6/2004 | Gellman |
| 6,755,843 B2 | 6/2004 | Chung et al. |
| 6,802,807 B2 | 10/2004 | Anderson et al. |
| 6,830,052 B2 | 12/2004 | Carter et al. |
| 6,911,003 B2 | 6/2005 | Anderson et al. |
| 6,932,759 B2 | 8/2005 | Kammerer et al. |
| 6,953,428 B2 | 10/2005 | Gellman et al. |
| 6,960,160 B2 | 11/2005 | Browning |
| 6,971,986 B2 | 12/2005 | Staskin et al. |
| 7,037,255 B2 | 5/2006 | Inman et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,112,171 B2 | 9/2006 | Rocheleau et al. |
| 7,131,943 B2 | 11/2006 | Kammerer |
| 7,175,591 B2 | 2/2007 | Kaladelfos |
| 7,198,597 B2 | 4/2007 | Siegel et al. |
| 7,204,802 B2 | 4/2007 | De Leval |
| 7,261,723 B2 | 8/2007 | Smith et al. |
| 7,267,645 B2 | 9/2007 | Anderson et al. |
| 7,291,104 B2 | 11/2007 | Neisz |
| 7,326,213 B2 | 2/2008 | Benderev et al. |
| 7,338,502 B2 | 3/2008 | Rosenblatt |
| 7,361,138 B2 | 4/2008 | Wagner et al. |
| 7,393,320 B2 | 7/2008 | Montpetit et al. |
| 7,410,460 B2 | 8/2008 | Benderef |
| 7,422,557 B2 | 9/2008 | Arnal et al. |
| 7,500,945 B2 | 3/2009 | Cox et al. |
| 7,556,598 B2 | 7/2009 | Rar |
| 7,611,454 B2 | 11/2009 | De Leval |
| 7,621,864 B2 | 11/2009 | Suslian et al. |
| 7,686,760 B2 | 3/2010 | Anderson et al. |
| 7,713,188 B2 | 5/2010 | Bouffier |
| 7,763,034 B2 | 7/2010 | Siegel et al. |
| 7,794,385 B2 | 9/2010 | Rosenblatt |
| 7,811,223 B2 | 10/2010 | Hodroff et al. |
| 7,828,715 B2 | 11/2010 | Haverfield |
| 7,833,235 B2 | 11/2010 | Chu |
| 8,709,021 B2 | 4/2014 | Chu et al. |
| 2001/0049467 A1 | 12/2001 | Lehe et al. |
| 2003/0065337 A1 | 4/2003 | Topper et al. |
| 2004/0106847 A1* | 6/2004 | Benderev ................. 600/37 |
| 2004/0225305 A1 | 11/2004 | Ewers et al. |
| 2004/0225385 A1 | 11/2004 | Takagi et al. |
| 2004/0230206 A1 | 11/2004 | Gellman et al. |
| 2005/0101834 A1 | 5/2005 | Merade |
| 2005/0245787 A1 | 11/2005 | Cox et al. |
| 2006/0058780 A1 | 3/2006 | Edwards et al. |
| 2006/0063968 A1 | 3/2006 | Anderson et al. |
| 2006/0069301 A1 | 3/2006 | Neisz et al. |
| 2006/0142637 A1 | 6/2006 | Gill |
| 2006/0173468 A1 | 8/2006 | Simmon et al. |
| 2006/0195007 A1 | 8/2006 | Anderson et al. |
| 2006/0217589 A1 | 9/2006 | Wan et al. |
| 2006/0235262 A1 | 10/2006 | Arnal et al. |
| 2006/0258898 A1 | 11/2006 | Montpetit et al. |
| 2006/0293554 A1 | 12/2006 | Crawford |
| 2007/0156012 A1 | 7/2007 | Tracey et al. |
| 2007/0173599 A1 | 7/2007 | Liu et al. |
| 2007/0173864 A1 | 7/2007 | Chu |
| 2007/0249936 A1 | 10/2007 | Deckman et al. |
| 2007/0249939 A1 | 10/2007 | Gerbi et al. |
| 2008/0004487 A1 | 1/2008 | Haverfield |
| 2008/0009914 A1 | 1/2008 | Buysman et al. |
| 2008/0021263 A1 | 1/2008 | Escude et al. |
| 2008/0076963 A1 | 3/2008 | Goria |
| 2008/0082121 A1 | 4/2008 | Chu |
| 2008/0091058 A1 | 4/2008 | Bosley et al. |
| 2008/0097329 A1 | 4/2008 | Hodroff et al. |
| 2008/0154087 A1 | 6/2008 | Wagner et al. |
| 2008/0167520 A1 | 7/2008 | Benderev |
| 2008/0188890 A1* | 8/2008 | Weitzner et al. ............ 606/205 |
| 2008/0200751 A1 | 8/2008 | Browning |
| 2008/0255563 A1 | 10/2008 | Farr et al. |
| 2009/0023978 A1 | 1/2009 | Arnal et al. |
| 2009/0048479 A1 | 2/2009 | Goria |
| 2009/0088599 A1 | 4/2009 | Zook et al. |
| 2009/0137861 A1 | 5/2009 | Goldberg et al. |
| 2009/0137862 A1 | 5/2009 | Evans et al. |
| 2009/0143637 A1 | 6/2009 | Raz et al. |
| 2009/0149700 A1 | 6/2009 | Garcia et al. |
| 2009/0177026 A1 | 7/2009 | Goldman |
| 2009/0216072 A1 | 8/2009 | Zipper |
| 2009/0221868 A1 | 9/2009 | Evans |
| 2009/0240104 A1 | 9/2009 | Ogdahl et al. |
| 2009/0259092 A1 | 10/2009 | Ogdahl et al. |
| 2009/0264698 A1 | 10/2009 | Arnal et al. |
| 2009/0276038 A1 | 11/2009 | Tremulis et al. |
| 2009/0287229 A1 | 11/2009 | Ogdahl |
| 2009/0306464 A1 | 12/2009 | Griguol |
| 2010/0030016 A1 | 2/2010 | Knoll |
| 2010/0113866 A1 | 5/2010 | Goldman |
| 2010/0113867 A1 | 5/2010 | Wiles et al. |
| 2010/0113868 A1 | 5/2010 | Goldman |
| 2010/0137888 A1 | 6/2010 | Wulc et al. |
| 2010/0191046 A1 | 7/2010 | Gobron et al. |
| 2010/0217069 A1 | 8/2010 | Meade et al. |

(56) References Cited

U.S. PATENT DOCUMENTS

| | | |
|---|---|---|
| 2010/0261952 A1 | 10/2010 | Montpetit et al. |
| 2010/0261955 A1* | 10/2010 | O'Hern et al. ............... 600/37 |
| 2010/0274074 A1* | 10/2010 | Khamis et al. ............... 600/37 |
| 2011/0160529 A1* | 6/2011 | Crawford ............... 600/37 |
| 2012/0158009 A1 | 6/2012 | Ostrovsky et al. |
| 2012/0232573 A1 | 9/2012 | Ostrovsky et al. |

FOREIGN PATENT DOCUMENTS

| | | |
|---|---|---|
| EP | 2001398 B1 | 5/2010 |
| EP | 2255733 A1 | 12/2010 |
| WO | 9639948 A1 | 12/1996 |
| WO | 2007109062 A2 | 9/2007 |
| WO | 2008097665 | 8/2008 |
| WO | 2009018372 A3 | 2/2009 |
| WO | 2012082638 A2 | 6/2012 |
| WO | 2012082638 A3 | 6/2012 |
| WO | 2013033373 A1 | 3/2013 |

OTHER PUBLICATIONS

Non-Final Office Action for U.S. Appl. No. 13/416,488, mailed on Feb. 21, 2014, 12 pages.

Final Office Action for U.S. Appl. No. 13/416,488, mailed on Aug. 29, 2014, 16 pages.

Restriction Requirement for U.S. Appl. No. 13/313,963, mailed on Feb. 27, 2014, 6 pages.

Non-Final Office Action for U.S. Appl. No. 13/313,963, mailed on Oct. 8, 2014, 7 pages.

Final Office Action for U.S. Appl. No. 13/313,963, mailed on Apr. 21, 2015, 10 pages.

Non-Final Office Action for U.S. Appl. No. 13/416,488, mailed on Jul. 6, 2015, 16 pages.

Non-Final Office Action for U.S. Appl. No. 13/313,963, mailed on Jul. 2, 2015, 8 pages.

* cited by examiner

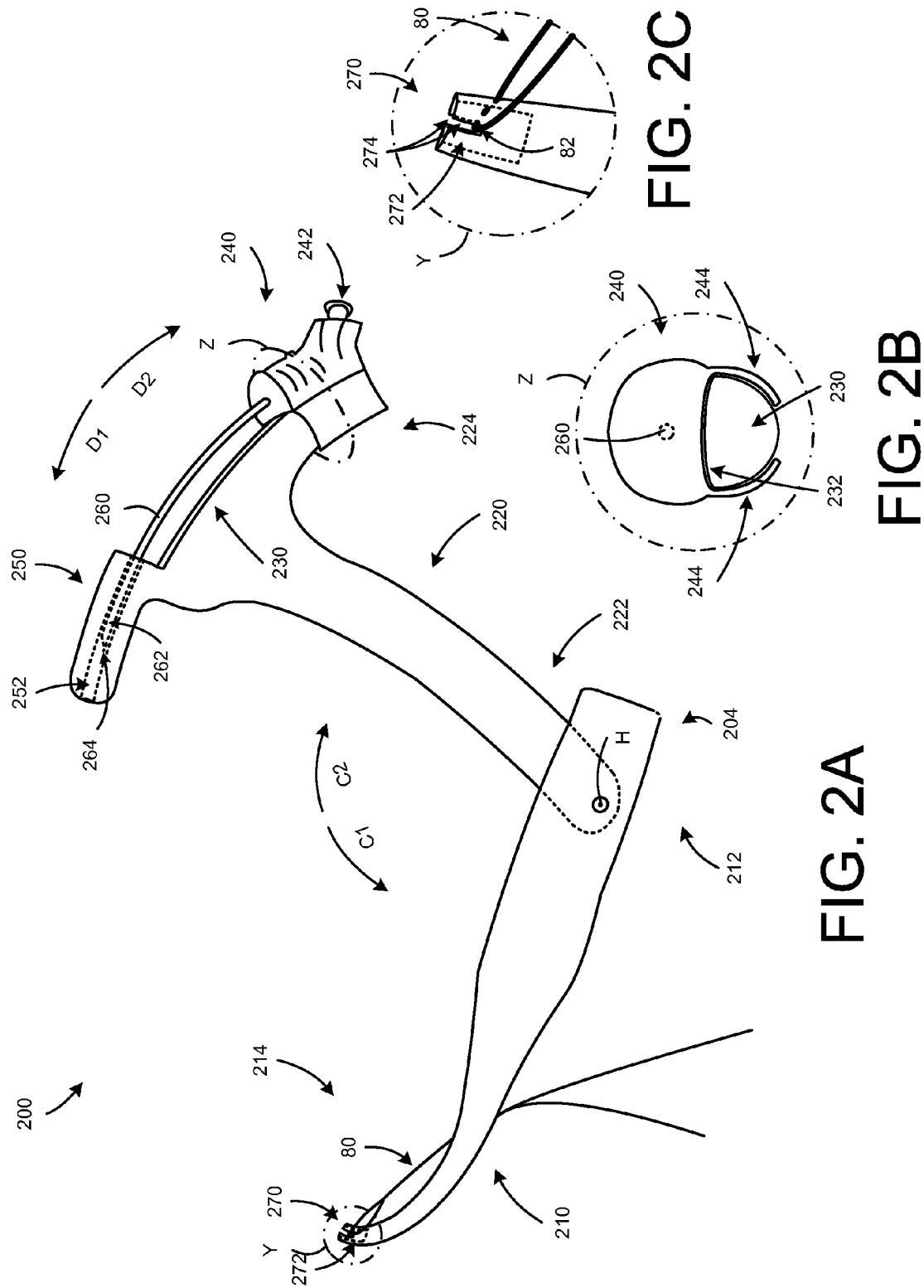

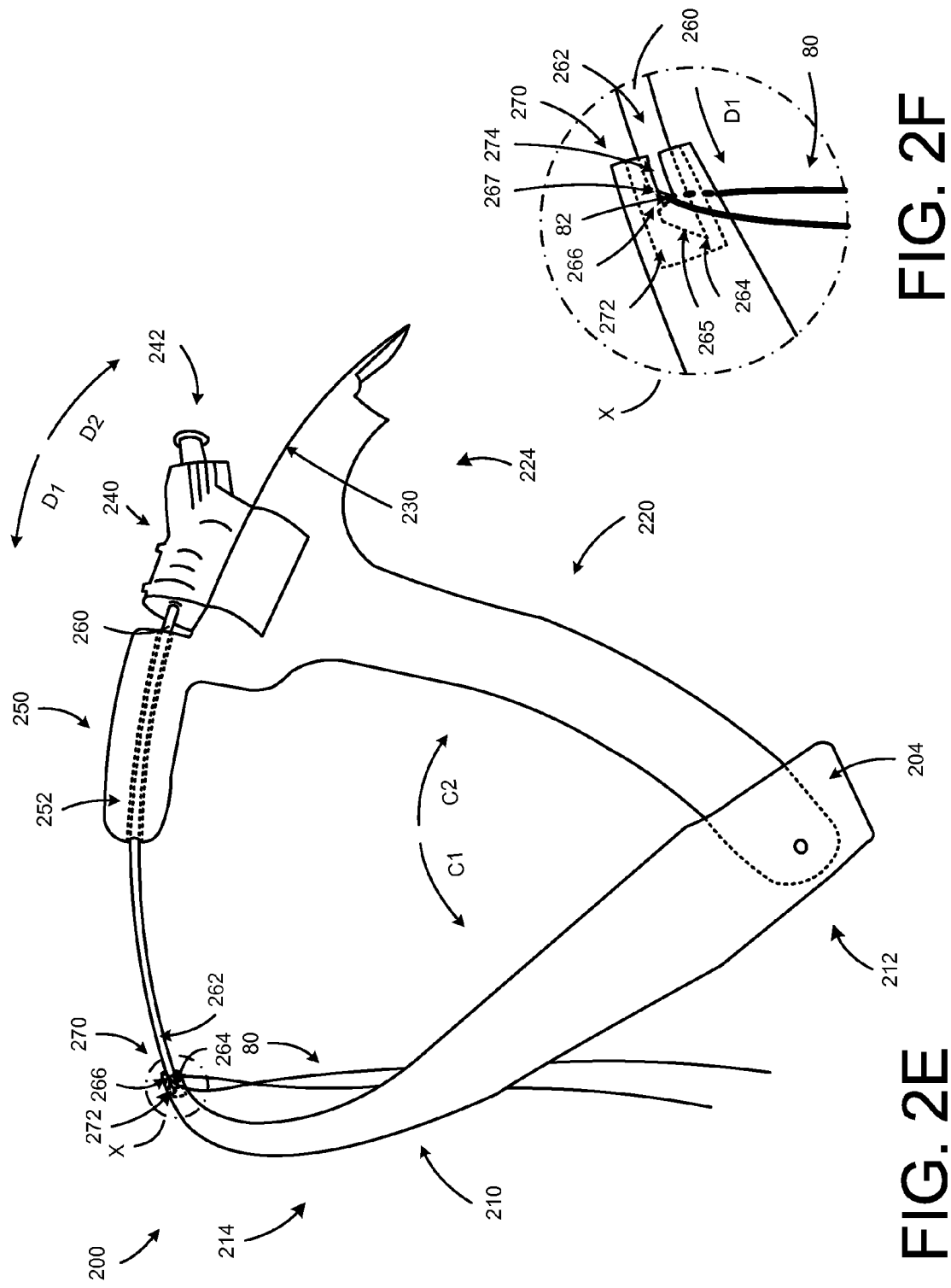

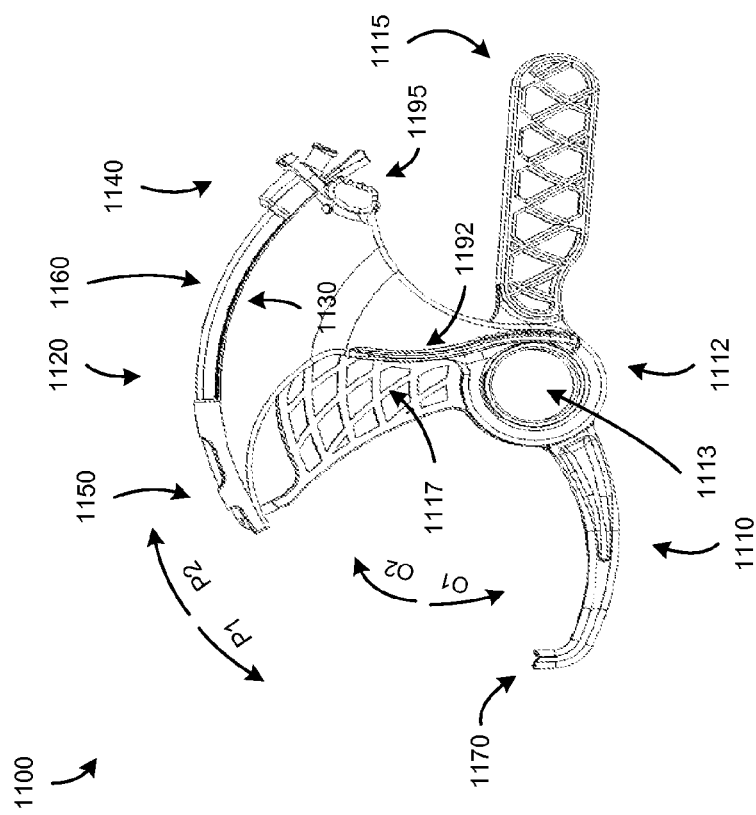
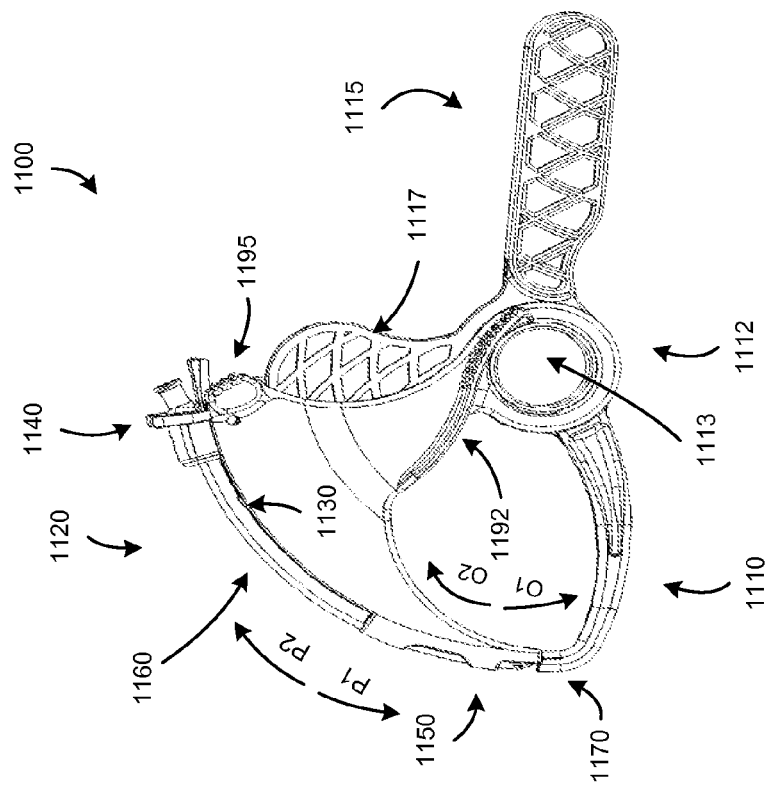

MULTI-ARM TOOL FOR DELIVERING IMPLANTS AND METHODS THEREOF

CROSS REFERENCE TO RELATED APPLICATION

This application is a Nonprovisional of, and claims priority to, U.S. Provisional Application No. 61/530,511, filed on Sep. 2, 2011, entitled "A MULTI-ARM TOOL FOR DELIVERING IMPLANTS AND METHODS THEREOF", which is incorporated by reference herein in its entirety.

TECHNICAL FIELD

This disclosure relates generally to medical devices and more particularly to medical devices that are configured to place or deliver implants within a body of a patient.

BACKGROUND

A variety of medical procedures are performed to provide support to portions of a body of a patient. For example, some medical procedures are performed to treat various pelvic dysfunctions, including procedures to treat urinary incontinence, and correcting various prolapse conditions such as uterine prolapse, cystoceles, rectoceles, and vaginal vault prolapse.

Some such medical procedures have included placing implants within the pelvic region of the patient. Some of the implants are delivered to the pelvic region of the patient through one or more vaginal incisions, and/or through exterior incisions in the patient.

Often such implants are delivered or placed within the body of the patient using an insertion or delivery tool. The insertion tools used to deliver the implants within a body of a patient typically include a curved portion and a sharp needle or point at one end. Some of the insertion tools used to deliver the implants can be uncontrollable and can deviate from the desired direction during the implantation process. Also, some of the insertion tools used to deliver the implants have large needles that can cause undesirable levels of trauma to tissues during the implantation process. Accordingly, complications, such as inadvertent tissue, nerve, bladder, or uretheral damage can occur during the implantation process. Such complications can also occur if the shape or curvature of the insertion tool is inappropriate for delivering the implant to the desired location within the body of the patient. Thus, it would be desirable to provide an insertion tool that may be used to deliver an implant to a location within a body of a patient without damaging tissue and/or adjacent nerves or organs in an undesirable fashion.

SUMMARY

In a general aspect, a medical device includes a receiving arm configured to be coupled to at least a portion of an implant, and a clamping arm having a proximal end coupled to the receiving arm and having a track at a distal end of the clamping arm. The medical device also includes a sliding component including a needle and configured to slidably move along the track of the clamping arm.

In another general aspect, a medical device includes a receiving arm configured to receive at least a portion of an implant, and a clamping arm coupled to the receiving arm and configured to move a track such that a distance between the track and the receiving arm is decreased. The medical device also includes a sliding component including a needle and configured to slidably move along the track such that the needle is moved toward the receiving arm.

In yet another general aspect, a method includes inserting at least a portion of a receiving arm of a medical device coupled to at least a portion of an implant into a body of a patient, and moving a sliding component along a track of a clamping arm such that a portion of a needle of the sliding component is moved into the body of the patient and is coupled to the portion of the implant.

BRIEF DESCRIPTION OF THE DRAWINGS

FIG. 2A is a side view of a medical device in an open configuration.
FIG. 2B is a cross-sectional view of a sliding component and a track of the medical device shown in FIG. 2A.
FIG. 2C illustrates a coupling mechanism of a receiving of arm of the medical device shown in FIG. 2A.
FIG. 2E illustrates the sliding component of the medical device shown in FIG. 2A in a deployed configuration.
FIG. 2F is a zoomed in view of a needle coupled to the coupling mechanism of the receiving arm of the medical device shown in FIG. 2E.
FIGS. 11A through 11I illustrate yet another medical device 1100 according to an embodiment.

DETAILED DESCRIPTION

Figure 1:
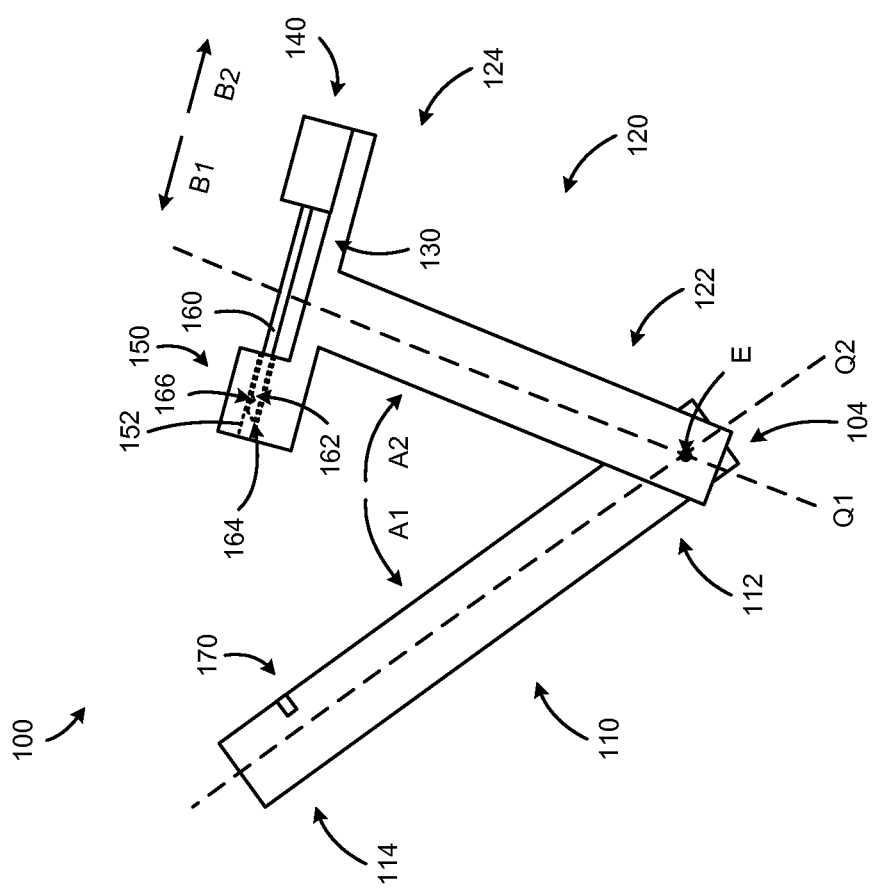
FIG. 1 is a schematic diagram of a medical device.

The devices and methods described herein are generally directed to insertion or delivery tools for placing implants within a body of a patient. The implants delivered with the insertion or delivery tools may be used in any portion of a body of a patient. In some embodiments, the implants include, but are not limited to, implants that are placed within a pelvic region of a patient. For example, the implants that may be placed with the disclosed insertion or delivery tools include posterior support implants, anterior support implants, and/or total pelvic floor repair implants. Such implants can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) and/or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. The insertion tools, implants, and procedures described herein may be used in a female patient and/or a male patient.

In some embodiments, the disclosed insertion or delivery tool(s) may be used to place an implant, for example, through a vaginal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or a posterior vaginal incision. In some embodiments, a procedure may include an exterior incision.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of an insertion tool or device as described herein refers to the end or portion of the device that is first inserted into a body of a patient during a medical procedure. The proximal end or portion is the end or portion of the device that is remains outside of the body of the patient during the insertion procedure (or if the entire device is inserted into the body of the patient during the delivery procedure, the proximal end portion is inserted into a body of the patient after the distal end or distal portion is inserted). The terms "trailing end" and "leading end" are also referred to herein and have similar meanings as proximal and distal, respectively. As used herein, the term "leading end" refers to the end of a device or apparatus that is inserted into a body first. The term "trailing end" refers to the end of the device or apparatus that remains outside of the body of the patient or is inserted into the body after the leading end.

Various embodiments of insertion or delivery tools are described herein. The insertion or delivery tool may be used to deliver a variety of different implants into the body of a patient and only some examples of implants are described herein.

FIG. 1 is a schematic diagram of a medical device 100. The medical device 100 is configured to be used as an insertion tool or delivery tool to implant or insert a bodily implant (not shown) into a body of a patient. In some embodiments, the medical device 100 is configured to be used to insert an implant into a body of a patient (e.g., a female patient, a male patient) using an outside-in approach (e.g., an outside-in approach via a vaginal incision in the body of the patient, an outside-in approach via a rectal incision in the body of the patient). The medical device 100 may be used to insert any type of implant into a body of a patient. In some embodiments, the medical device 100 can be configured to place an implant into a pelvic region of a patient. Specifically, in some embodiments, the medical device 100 is configured to place an implant through an obturator muscle and/or a membrane of a patient.

As shown in FIG. 1, the medical device 100 has a receiving arm 110 and a clamping arm 120. The clamping arm 120 is coupled (e.g., movably coupled, slidably coupled, rotatably coupled, hingedly coupled) to the receiving arm 110 so that the clamping arm 120 and the receiving arm 110 can be moved towards one another. Specifically, in this embodiment, a proximal portion 122 of the clamping arm 120 is rotatably coupled to a proximal portion 112 receiving arm 110 to collectively define a hinge portion 104 of the medical device 100. As shown in FIG. 1, the receiving arm 110 and the clamping arm 120 are rotatably coupled (e.g., hingedly coupled using a pin, a screw, and/or so forth) about an axis E (coming out of the figure).

As shown in FIG. 1, the clamping arm 120 can be moved (e.g., rotatably moved) in a direction A1 (e.g., a counterclockwise direction) toward the receiving arm 110 and/or the receiving arm 110 can be moved (e.g., rotatably moved) in a direction A2 (e.g., a clockwise direction) toward the clamping arm 120 so that a distance between at least a portion of the receiving arm 110 and at least a portion of the clamping arm 120 is decreased (e.g., decreased to approximately 3 inches (3.81 centimeters (cm)), decreased to less 4 inches (10.16 cm), decreased to less 2 inches (5.08 cm)). The clamping arm 120 can be moved (e.g., rotatably moved) in the direction A2 (e.g., clockwise direction) away from the receiving arm 110 and/or the receiving arm 110 can be moved (e.g., rotatably moved) in the direction A1 (e.g., counterclockwise direction) away from the clamping arm 120 so that a distance between at least a portion of the receiving arm 110 and at least a portion of the clamping arm 120 is increased (e.g., increased to greater than 1.5 inches (3.81 cm), increased to greater 2 inches (5.08 cm), increased to greater 4 inches (10.16 cm), increased to approximately 5 inches (12.7 cm)).

In the embodiment shown in FIG. 1, the medical device 100 is in an open configuration. The medical device 100 can be moved from the open configuration to a clamped configuration (or closed configuration) by moving the clamping arm 120 toward the receiving arm 110 (or vice versa). After being moved to the clamped configuration, the medical device 100 can be moved from the clamped configuration (or closed configuration) to the open configuration by moving the clamping arm 120 away from the receiving arm 110 (or vice versa).

As shown in FIG. 1, a distal portion 124 of the clamping arm 120 includes a sliding component 140 configured to slidably move on a track 130 (which can be referred to as a track portion or as a track portion of the clamping arm 120) of the clamping arm 120. The sliding component 140 is coupled to (or includes) a needle 160 configured to slidably move within a lumen 152 within a guide 150 (the guide 150 can be referred to as a guide portion). In some embodiments, the needle 160 can have a distal portion 162, and the distal portion 162 can have a distal tip 164. The sliding component 140 is configured to slidably move in direction B1 along the track 130 so that a sliding component 140 is moved toward the guide 150. The sliding component 140 is also configured to slidably move in direction B2 (after being moved in direction B1) along the track 130 so that the sliding component is moved away from the guide 150.

The receiving arm 110 includes a coupling mechanism 170 on a distal portion 114 the receiving arm 110. At least a portion of an implant (not shown) configured to be inserted into a body of a patient can be coupled to the coupling mechanism 170. In some embodiments, the coupling mechanism 170 can be, or can include, an opening, a slot, a hook, a latch, a recess, and/or so forth. In some embodiments, the slot can be, for example, an L-shaped slot or a T-shaped slot.

The sliding component 140 (and needle 160) as illustrated in FIG. 1, is in a stowed configuration. The sliding component 140 can be moved from the stowed configuration to a deployed configuration (not shown) when the sliding component 140 is moved in direction B1 along the track 130. The sliding component 140 can be moved from the deployed configuration to the stowed configuration by slidably moving the sliding component 140 in direction B2 along the track away from the guide 150.

When in the stowed configuration, a distal portion 162 of the needle 160 is disposed within (e.g., in a position disposed within) the lumen 152 of the guide 150 or is in a position proximal to (on the right side of) the guide 150. When in the deployed configuration, the distal portion 162 of the needle 160 is moved outside of (e.g. is moved to position outside of) the lumen 152 of the guide 150 so that the distal portion 162 of the needle 160 is distal to (on the left side of) the guide 150. In some embodiments, the stowed configuration can be referred to as a refracted configuration, and the deployed configuration can be referred to as an extended configuration.

In some embodiments, the sliding component 140 (and needle 160) can have many different deployed configurations and stowed configurations. For example, the sliding component 140 (and needle 160) can be moved along direction B1 from a first deployed configuration to a second deployed configuration. A portion of the needle 160 disposed outside of the guide 150 when in the first deployed configuration can be shorter than a portion of the needle 160 disposed outside of the guide 150 when the sliding component 140 is in the second deployed configuration. In some embodiments, the sliding component 140 (and the needle 160) can be moved along direction B2 from the second deployed configuration to the first deployed configuration. As another example, the sliding component 140 (and the needle 160) can be moved along direction B2 from a first stowed configuration to a second stowed configuration. The distal portion 162 of the needle 160 may be disposed within the guide 150 when the sliding component 140 is in the first stowed configuration and the distal portion 162 of the needle 160 may be disposed in a proximal position outside of the guide 150 when the sliding component 140 is in the second stowed configuration. In some embodiments, the sliding component 140 (and the needle) can be moved along direction B1 from the second stowed configuration to the first stowed configuration.

The sliding component 140 (and needle 160) can be configured so that the sliding opponent 140 can be moved between stowed configurations and/or deployed configurations when the medical device 100 is in the clamped configuration (or closed configuration) or the open configuration. For example, the medical device 100 can be moved from an open configuration to a clamped configuration, while the sliding component 140 is in a stowed configuration. After the clamping arm 120 is moved toward the receiving arm 110 along direction A1 (or the receiving arm 110 is moved toward the clamping arm 120 along direction A2) so that the medical device 100 is in the clamped configuration (or closed configuration), the sliding component 140 (and needle 160) can be slidably moved along direction B1 from the stowed configuration to a deployed configuration. As another example, the medical device 100 can be moved from a clamped configuration to an open configuration while the sliding component 140 is in a deployed configuration. After the clamping arm 120 is moved away from the receiving arm 110 along direction A2 so that the medical device 100 is in the open configuration, the sliding component 140 (and needle 160) can be slidably moved along direction B2 from the deployed configuration to a stowed configuration.

In some embodiments, when the sliding component 140 is in the deployed configuration, at least a portion of the needle 160 (e.g., the distal portion 162 of the needle 160) can contact, or can be moved into relatively close proximity, to at least a portion of the receiving arm 110. In some embodiments, when the sliding component 140 is in the deployed configuration, at least a portion of the needle 160 can contact and/or can be moved inside of at least a portion of the coupling mechanism 170 of the receiving arm 110. For example, if the coupling mechanism 170 defines, or includes, a cavity, at least a portion of the needle 160 can be moved inside of the cavity when the sliding component 140 is in the deployed configuration.

In some embodiments, when the sliding component 140 is in the deployed configuration, at least a portion of the needle 160 (e.g., at least a portion of the distal portion 162 of the needle 160) can contact and/or can be coupled to (e.g., can engage) at least a portion of an implant coupled to the coupling mechanism 170 of the receiving arm 110. Specifically, the needle 160 can have a coupling mechanism 166 at a distal portion 162 of the needle 160. In some embodiments, the coupling mechanism 166 can be, or can include, an opening, a slot, a hook, a latch, a recess, and/or so forth. In some embodiments, the slot can be, for example, an L-shaped slot or a T-shaped slot.

For example, when the sliding component 140 is moved to the deployed configuration (and the medical device 100 is in the clamped configuration), the coupling mechanism 166 of the distal portion 162 of the needle 160 can be coupled to an implant coupled to the coupling mechanism 170 of the receiving arm 110. When the sliding component 140 is moved to the stowed configuration after coupling mechanism 166 of the distal portion 162 is coupled to the implant, the implant can be decoupled from (e.g., extracted from, removed from) the coupling mechanism 170 of the receiving arm 110. In some embodiments, the sliding component 140 can be moved to the deployed configuration to retrieve the implant from the coupling mechanism 170 of the receiving arm 110. In some embodiments, the sliding component 140 of the clamping arm 120 can be moved to the deployed configuration to retrieve at least a portion of an implant coupled to the coupling mechanism 170 of the receiving arm 110 after the medical device 100 is moved to the clamped configuration.

In some embodiments, the coupling mechanism 166 of the distal portion 162 can be actuated, or triggered to be actuated, so that the coupling mechanism 166 can be coupled to the implant. In some embodiments, the coupling mechanism 170 can be actuated, or triggered to be actuated, to release the implant from the coupling mechanism 170.

In some embodiments, the distal tip 164 of the needle 160 can be configured to cut or pierce a bodily tissue. For example, in some embodiments, the distal tip 164 can include a sharp portion. In some embodiments, the distal tip 164 can define a blunt end. In some embodiments, the distal tip 164 can define a dilating end configured to dilate a tissue of a patient.

As mentioned above, in some embodiments, the medical device 100 may be used to insert an implant (e.g., a surgical implant) (not shown) into a pelvic region of a patient. Specifically, the medical device 100 can be used to insert an implant into a pelvic region of a patient using an outside-in method.

First, the implant can be coupled to, or associated with, the coupling mechanism 170 included in the distal portion 114 of the receiving arm 110 of the medical device 100. In some embodiments, the implant can be coupled to, or associated with, the coupling mechanism 170 of the medical device 100 when the medical device 100 is in the open configuration and/or when the medical device 100 is in the clamped configuration. An example of an implant that can be used with the medical device 100 is shown in connection with FIG. 3.

After the implant has been coupled to, or associated with, the coupling mechanism 170 of the receiving arm 110, the receiving arm 110 of the medical device 100 (e.g., at least a portion of the distal portion 114 of the receiving arm 110) can be inserted into a body of a patient. In some embodiments, the receiving arm 110 of the medical device 100 may be inserted into the pelvic region of the patient through an anterior vaginal incision (i.e., via an outside-in approach). In some embodiments, the medical device 100 can be inserted into the body of the patient such that the receiving arm 110 is moved along an edge of, or in close proximity to, an edge of a bone (e.g., a pelvic bone) of the patient.

In some embodiments, the medical device 100 can be in the open configuration (or moved to the open configuration) shown in FIG. 1 when at least the distal portion 114 (which is coupled to or associated with the implant) of the receiving arm 110 of the medical device 100 is inserted into the body of the patient. Specifically, the medical device 100 can be in the open configuration shown in FIG. 1 so that the clamping arm 120 may remain outside of the body of the patient (e.g., outside of a skin of the patient).

When the receiving arm 110 of the medical device 100 is inserted into the body of the patient, the sliding component 140 can be in the stowed configuration. The sliding component 140 can be in the stowed configuration so that the distal tip 164 of the needle 160 may not come in contact with a bodily tissue of a patient (because the distal tip 164 will be disposed within lumen 152 of the guide 150).

After the receiving arm 110 has been inserted into the body of the patient, the medical device 100 can be moved to the clamped configuration. Specifically, the clamping arm 120 and the receiving arm 110 can be moved towards one another so that a distance between, for example, the track 130 and the coupling mechanism 170 may be decreased. When moved to the clamped configuration, the guide 150 of the clamping arm 120 of the medical device 100 may come in contact with the body of the patient. In some embodiments, a physician may apply a force (along direction A1) to the clamping arm 120 so that the medical device 100 can be changed to the clamped configuration.

In some embodiments, the medical device 100 may be placed in a desirable location with respect to, for example an obturator muscle and/or another target membrane of a patient before being moved to the clamped configuration. Specifically, the medical device 100 may be placed so that the guide 150 may be disposed on one side of an obturator muscle (and/or another target membrane) of the patient and the coupling mechanism 170 (which is coupled to or associated with the implant) may be disposed on another side of the obturator muscle (and/or another target membrane) of the patient. Accordingly, when the sliding component 140 is moved to the deployed configuration, the distal tip 164 of the needle 160 will be slidably moved through the lumen 152 of the guide 150 and pierce through the obturator muscle (and/or another target membrane) of the patient and toward the coupling mechanism 170.

After the medical device 100 (e.g., the receiving arm 110 and the clamping arm 120) is in a clamped configuration in a desirable location around, for example, the obturator muscle (and/or another target membrane) of the patient, the sliding component 140 can be moved from the stowed configuration to the deployed configuration (along direction B1) so that the distal tip 164 of the needle 160 can be deployed (e.g., extended out of the lumen 152 of the guide 150) and pierce through the obturator muscle (and/or another target membrane). The distal tip 164 of the needle 160 may be moved until the coupling mechanism 166 is coupled to at least a portion of the implant (e.g., a tether of the implant, association members of the implant) coupled to, or associated with, the coupling mechanism 170 of the receiving arm 110.

During a medical procedure, the coupling mechanism 170 of the receiving arm 110 (and the implant coupled thereto) may not be visible to a physician using the medical device 100 when the coupling mechanism 170 of the receiving arm 110 (and the implant coupled thereto) are disposed within the body of the patient. Even though the coupling mechanism 170 of the receiving arm 110 (and the implant coupled thereto) may not be visible to the physician using the medical device 100 when the sliding component 140 is moved to the deployed configuration, the track 130 and/or the guide 150 may be collectively configured so that the coupling mechanism 166 of the needle 160 may be coupled to at least a portion of the implant in a desirable fashion. In some embodiments, the needle 160 may be configured (e.g., configured with a stiffness) so that the coupling mechanism 166 of the needle 160 coupled to at least a portion of the implant without deflecting away from the implant in an undesirable way.

After the coupling mechanism 166 of the needle 160 is coupled to at least the portion of the implant (e.g., the tether of the implant, association members of the implant), the sliding component 140 can be moved in direction B2 from the deployed configuration to a stowed configuration so that the portion of the implant may be withdrawn from the body of the patient. In other words, the coupling mechanism 166 of the needle 160 can be retracted, while coupled to the implant (or at least a portion thereof). Thus, the portion of the implant can be extracted from the coupling mechanism 170 of the receiving arm 110 and the portion of the implant can be moved from a position inside of the body of the patient to a position outside of the body of the patient using the sliding component 140 of the clamping arm 120. The implant can be decoupled from (e.g., extracted from, removed from) the coupling mechanism 166 by, for example, a physician after the sliding component 140 is moved to the stowed configuration.

Although the portion of the implant is withdrawn from body of the patient, another portion of the implant (e.g., a sling portion of the implant) may remain within the body of the patient. In some embodiments, the portion of the implant withdrawn from the body of the patient may be used to adjust a location and/or tension of the portion of the implant remaining within the body of the patient.

Because certain tissues of a patient (e.g., an obturator muscle) can be relatively stiff and/or relatively difficult to pierce, the guide 150 of the clamping arm 120 can function as a support for the needle 160 as the distal tip 164 is moved through the tissue(s). Specifically, the guide 150 of the clamping arm 120 can be made of a relatively rigid material that can prevent (or substantially prevent) the needle 160 from bending in an undesirable fashion. In some embodiments, the guide 150 can support the needle 160 while the distal tip 164 is moved through a tissue so that the needle 160 may not be deformed inelastically. Because the distal end (e.g., left side) of the guide 150 can be contacting or close to tissue that will be pierced by at least a portion of the distal tip 164 of the needle 160, a length of the portion of the distal portion 162 can be zero, or nearly zero, when the distal tip 164 contacts the tissue as the sliding mechanism 140 is moved to the deployed configuration.

The track 130 is configured so that the sliding component 140 can be slidably moved on the track 130. In some embodiments, the track 130 can be, or can include, a slot or groove into which the sliding component 140 can be inserted and slidably moved. In some embodiments, the track 130 can include a member (e.g., a rod) along which the sliding component 140 can slidably move. In some embodiments, at least a portion of the sliding component 140 can be disposed around (e.g., at least partially around), or otherwise coupled to, the member. In some embodiments, the sliding component 140 and/or the track 130 can include rolling devices such as wheels or ball-bearings that can facilitate translational movement (e.g., facilitate relatively smooth translational movement) of the sliding component 140 along the track 130. A cross-sectional view of an example of a track is shown and described in connection with FIG. 2B.

In some embodiments, the needle 160 has a circular cross-sectional shape (or outer profile). In some embodiments, the needle 160 can have a different shape than a circular cross-sectional shape. In some embodiments, the needle 160 can have a cross-sectional shape (or outer profile) of any type of polygon. For example, the needle 160 can have a square or a rectangular cross-sectional shape (or outer profile). In some embodiments, the needle 160 can have a tapered shaped and/or a tapered portion (e.g., tapered from a proximal portion to a distal portion). In such embodiments, the needle 160 can have a varying diameter.

In some embodiments, the lumen 152 of the guide 150 can have a cross-sectional shape of any type of polygon. For example, the lumen 152 can have a square or rectangular cross-sectional shape (or outer profile) within which the needle 160 can be disposed. In some embodiments, the lumen 152 can have a tapered shaped and/or a tapered portion (e.g., tapered from a proximal portion to a distal portion).

In some embodiments, the needle 160 has a portion of a surface with a cross-sectional shape (or outer profile) that matches a portion of an inner surface of the lumen 152 of the guide 150. In some embodiments, the needle 160 can have a shape that does not match (e.g., is different from) a cross-sectional shape of the lumen 152 of the guide 150.

As shown in FIG. 1, clamping arm 120 is aligned along a longitudinal axis Q1 and the receiving arm 110 is aligned along a longitudinal axis Q2. As shown in FIG. 1, an acute angle is defined by the longitudinal axis Q1 of clamping arm 120 and the longitudinal axis Q2 of receiving arm 110 when the medical device 100 is in the open configuration. A second acute angle, that is smaller than the first acute angle, is defined by the longitudinal axis Q1 of clamping arm 120 and the longitudinal axis Q2 of the receiving arm 110 when the clamping arm 120 is moved towards the receiving arm 110 to define the clamped configuration of the medical device 100. Thus, an angle between longitudinal axis Q1 of the clamping arm 120 and the longitudinal axis Q2 of the receiving arm 110 decreases when the medical device 100 is moved from the open configuration to the clamped configuration. It follows that the angle between longitudinal axis Q1 of the clamping arm 120 and the longitudinal axis Q2 of the receiving arm 110 increases when the medical device 100 is moved from the clamped configuration to the open configuration. Thus, the medical device 100 can be reversibly moved to/from the clamped configuration or the open configuration.

Although not shown in FIG. 1, in some embodiments, the medical device 100 can have one or more locking mechanisms configured to removably (e.g., releasably) lock the medical device 100 into one or more clamped configurations and/or one or more open configurations. In some embodiments, the medical device 100 can also have one or more locking mechanisms configured to removably lock the sliding component 140 into one or more stowed configurations and/or one or more deployed configurations along the track 130. More details related to locking mechanisms are discussed in connection with, for example, FIGS. 4 through 6.

In some embodiments, movement of the sliding component 140 along the track 130 may be limited based on a position of the receiving arm 110 with respect to the clamping arm 120. For example, the movement of the sliding component 140 along the track 130 may be limited to a particular position along the track 130 when the medical device 100 is in a particular clamped configuration. More details related to movement of a sliding component being limited are discussed in connection with, for example, FIGS. 5 and 6.

In some embodiments, the medical device 100 can include an indicator mechanism configured to indicate a position of at least a portion of the receiving arm 110 with respect to a portion of the clamping arm 120. For example, the medical device 100 can include an indicator mechanism configured to indicate that the distal tip 164 of the needle 160 is disposed within the coupling mechanism 170 when the sliding component 140 is in a specified position along the track 130. As another example, medical device 100 can include an indicator mechanism configured to represent a distance (e.g., relative distance) between at least a portion of the receiving arm 110 (e.g., the coupling mechanism 170 of the receiving arm 110) and at least a portion of the clamping arm 120 (e.g., a distal portion of the track 130). In some embodiments, because the coupling mechanism 170 of the receiving arm 110, and an implant coupled thereto, may not be visible to the physician when using the medical device 100, the medical device 100 can include one or more indicators (and/or indicator mechanisms) configured to assist a physician in inserting the implant into a body of a patient in a desirable fashion. More details related to indicators are described in connection with, for example, FIGS. 5 and 6.

Although not shown in FIG. 1, in some embodiments, the medical device 100 can be configured so that the medical device 100 is biased towards one or more open configurations (such as the open configuration shown in FIG. 1) or one or more the clamped configuration. In such embodiments, a biasing mechanism such as a spring mechanism, a gear mechanism, and/or so forth, can be disposed between receiving arm 110 (or a portion thereof) and clamping arm 120 (or portion thereof) to cause the medical device 100 to be biased toward one or more open configurations and/or one or more clamped configurations. In some embodiments, the biasing mechanism can be coupled to the medical device 100 at, or around, the hinge portion 104.

If biased toward the open configuration, a force (e.g., a constant force) may be applied (e.g., applied against the receiving arm 110 and/or the clamping arm 120) to move the receiving arm 110 and the clamping arm 120 towards one another so that the medical device 100 can be changed to the clamped configuration. When the force is no longer applied, the receiving arm 110 and the clamping arm 120 can be moved away from one another by the biasing mechanism.

If biased towards the clamped configuration, a force (e.g., a constant force) may be applied (e.g., applied against the receiving arm 110 and/or the clamping arm 120) to move the receiving arm 110 in the clamping arm 120 away from one another so that the medical device 100 can be changed to the open configuration. When the force is no longer applied, the receiving arm 110 and the clamping arm 120 can be moved towards one another in response to the biasing mechanism.

Although not shown in FIG. 1, in some embodiments, the sliding component 140 can be configured so that the sliding component 140 is biased toward one or more stowed configurations (such as the stowed configuration shown in FIG. 1) or one or more deployed configurations. In such embodiments, a biasing mechanism such as a spring mechanism, a gear mechanism, and/or so forth, can be coupled to the track 130, the sliding component 140, the guide 150, and/or so forth. As a specific example, the spring may be disposed between the sliding component 140 and the guide 150 to cause the sliding component 140 to be biased towards the stowed configuration shown in FIG. 1.

If biased towards the stowed configuration, a force (e.g., a constant force) may be applied (e.g., applied against the sliding component 140) to move the sliding component 140 along direction B1 towards the guide 150 along the track 130 so that the sliding component 140 can be changed to the deployed configuration. When the force is no longer applied, the sliding component 140 can be moved back to the stowed configuration by the biasing mechanism. Similarly, if biased towards the deployed configuration, a force (e.g., a constant force) may be applied (e.g., applied against the sliding component 140) to move the sliding component 140 along direction B2 away from the guide 150 along the track 130 so that the sliding component 140 can be changed to the stowed configuration. When the force is no longer applied, the sliding component 140 can be moved back to the deployed configuration by the biasing mechanism.

In some embodiments, at least a portion of the needle 160 can be formed of a flexible material. For example, a portion of the needle 160 that remains disposed within the guide 150 when in the stowed configuration and in the deployed configuration can be configured to flex or bend. In some embodiments, at least a portion of the needle 160 that is made of a flexible material can be biased to a specified position and/or curvature. In some embodiments, at least a portion of the needle 160 can be formed of a flexible material so that a portion of the needle 160 can conform to a curvature of the guide 150 (e.g., a varying curvature), if curved, as the needle 160 is slidably moved within the guide 150.

The medical device 100, or portions thereof, can be made of various types of materials such as a polymer-based material (e.g., a polycarbonate material), a metal (e.g., stainless steel), and/or so forth. In some embodiments, any portion of the medical device 100 can be formed of a biocompatible material. In some embodiments, needle 160 can be formed of, for example, a polymer-based material, a stainless steel material (e.g., surgical grade stainless steel), and/or so forth.

FIG. 2A is a side view of a medical device 200 in an open configuration. The medical device 200 is configured to be used as an insertion tool or delivery tool to implant or insert a bodily implant (not shown) into a body of a patient. In some embodiments, the medical device 200 is configured to be used to insert an implant into a body of a patient (e.g., a male patient, a female patient) using an outside-in approach (e.g., an outside-in approach via a vaginal incision in the body of the patient). The medical device 200 may be used to insert any type of implant into a body of a patient. In some embodiments, the medical device 200 can be configured to place an implant into a pelvic region of a patient. Specifically, in some embodiments, the medical device 200 is configured to place an implant through an obturator muscle and/or a membrane of a patient.

As shown in FIG. 2A, the medical device 200 has a receiving arm 210 and a clamping arm 220. The clamping arm 220 is coupled (e.g., rotatably coupled, hingedly coupled) to the receiving arm 210 so that the clamping arm 220 and the receiving arm 210 can be moved towards one another. Specifically, a proximal portion 222 of the clamping arm 220 is rotatably coupled to a proximal portion 212 of the receiving arm 210 to collectively define a hinge portion 204 of the medical device 200. In this embodiment, at least a portion of the proximal portion 222 of the clamping arm 220 is disposed inside of the receiving arm 210. In some embodiments, at least a portion of the proximal portion 212 of the receiving arm 210 may be disposed inside of the clamping arm 220. In some embodiments, a portion of the clamping arm 220 may not be disposed within a portion of the receiving arm 210.

As shown in FIG. 2A, the clamping arm 220 can be moved (e.g., rotatably moved) in a counterclockwise direction C1 towards the receiving arm 210 and/or the receiving arm 210 can be moved (e.g., rotatably moved) in a clockwise direction C2 towards from the clamping arm 220 so that a distance between at least a portion of the receiving arm 210 (e.g., a coupling mechanism 270 of the receiving arm 210) and at least a portion of the clamping arm 220 (e.g., a track 230 of the clamping arm 220) is decreased. The clamping arm 220 can be moved (e.g., rotatably moved) in a clockwise direction C2 away from the receiving arm 210 and/or the receiving arm 210 can be moved (e.g., rotatably moved) in a counterclockwise direction C1 away from the clamping arm 220 so that a distance between at least a portion of the receiving arm 210 (e.g., the coupling mechanism 270 of the receiving arm 210) and at least a portion of the clamping arm 220 (e.g., the track 230 of the clamping arm 220) is increased. As shown in FIG. 2A, the receiving arm 210 and the clamping arm 220 are hingedly coupled (e.g., hingedly coupled using a pin, a screw, and/or so forth) about an axis H (coming out of the figure).

Figure 2D:
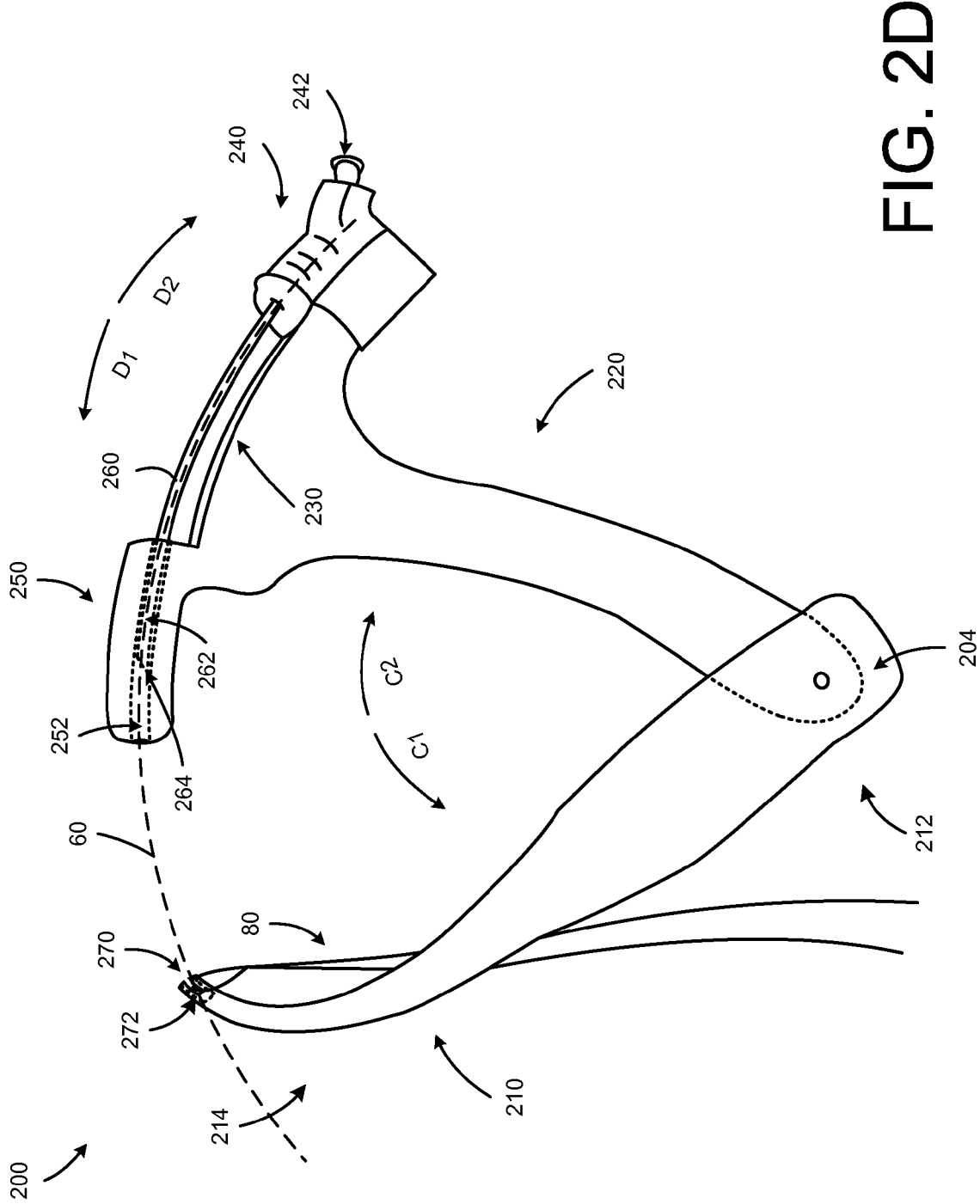
FIG. 2D is a side view of the medical device shown in FIG. 2A in a clamped configuration.

FIG. 2D is a side view of the medical device 200 shown in FIG. 2A in a clamped configuration. The medical device 200 can be moved from the open configuration shown in FIG. 2A to a clamped configuration shown in FIG. 2D by moving the clamping arm 220 toward the receiving arm 210 (and/or vice versa). In some embodiments, the medical device 200 can be moved to the clamped configuration shown in FIG. 2D after at least a portion of the receiving arm 210 has been inserted into a body of a patient (e.g., into a vaginal region of the patient) while the medical device 200 is in the open configuration shown in FIG. 2A. In some embodiments, a distal portion of (e.g., a left portion of) the guide 250 may be pushed against (e.g., compressed against) a tissue (e.g., a skin layer) of the patient when the medical device 200 is moved to the clamped configuration after the portion of the receiving arm 210 has been inserted into the body of the patient. In some embodiments, the distal portion of the guide 250 may be pushed to compress the tissue of the patient (disposed between the receiving mechanism 270 and the guide 250) when the medical device 200 is moved to the clamped configuration so that a distance that the distal tip 264 travels (e.g., moves) when the sliding component 240 is moved from the stowed configuration (shown in FIG. 2D) to the deployed configuration (shown in FIG. 2E) is shorter than a distance that the distal tip 264 travels (e.g., moves) when the sliding component 240 is moved from the stowed configuration to the deployed configuration if the tissue of the patient is not compressed when the medical device 200 is in the clamped configuration. After being moved to the clamped configuration, the medical device 200 can be moved from the clamped configuration (shown in FIG. 2D) to the open configuration (shown in FIG. 2A) by moving the clamping arm 220 away from the receiving arm 210 (and/or vice versa).

As shown in FIG. 2A, a distal portion 224 of the clamping arm 220 includes a sliding component 240 configured to slidably move along the track 230 (which can be referred to as a track portion) of the clamping arm 220. The sliding component 240 is coupled to (or includes) a needle 260 configured to slidably move within a lumen 252 of a guide 250 (the guide 250 can be referred to as a guide portion). In some embodiments, the needle 260 can have a distal portion 262 and the distal portion 262 can have a distal tip 264. The sliding component 240 is configured to slidably move in direction D1 along the track 230 so that a sliding component 240 is moved toward the guide 250. The sliding component is also configured to slidably move in direction D2 (after being moved in direction D1) along the track 230 so that the sliding component is moved away from the guide 250.

FIG. 2B is a cross-sectional view of the sliding component 240 and the track 230 shown in FIG. 2A. Specifically the cross-sectional view shown in FIG. 2B is cut along the area Z. In this embodiment, the sliding component 240 includes sliding members 244 that wrap at least partially around the track 230 so that the sliding component 240 may remain coupled to (e.g., may not become decoupled from) the track 230. The track 230 has a top surface 232 along which the sliding component 240 can slidably move. In some embodiments, the top surface 232 of the track 230 can be a curved surface, a flat surface, and/or so forth. In some embodiments, the track 230 can have a cross-sectional shape (or outer profile) of any type of polygon. For example, the track 230 can have a square or a rectangular cross-sectional shape (or outer profile). In some embodiments, the track 230 can have a tapered shaped and/or a tapered portion (e.g., tapered from a proximal portion to a distal portion).

As shown in FIG. 2A, the track 230 and needle 260 are curved. As shown in FIG. 2A, the track 230 and the needle 260 have a concave curvature around the hinge portion 204 of the medical device 200. In other words the concave portion (or inner surface of the concave portion) of the curvature of the track 230 and the curvature of the needle 260 face towards the hinge portion 204 of the medical device 200. Thus, a radius of curvature of the track 230 and a radius of curvature of the needle 260 is approximately aligned along a longitudinal axis of the clamping arm 220. Also, a radius of curvature of the track 230 and a radius of curvature of the needle 260 are on the same side as the hinge portion 204 of the medical device 200. In this embodiment, the centroid of the track 230 and of the needle 260 is approximately at the axis H where the receiving arm 210 is hingedly coupled to the clamping arm 220. Thus, the radius of curvature of the track 230 extends between (e.g., extends approximately between) the track 230 and the axis H, and radius of curvature of the needle 260 extends between (e.g., extends approximately between) the needle 260 and the axis H.

In some embodiments, the coupling mechanism 270 of the receiving arm 210 can be aligned with the needle 260 and/or the sliding component 240 so that the distal portion 262 (e.g., distal tip 264) of the needle 260 will come into close proximity to (or will be inserted into) the coupling mechanism 270 regardless of the position of (or over a range of positions of) the coupling mechanism 270 with respect to the sliding component 250 and/or the needle 260. For example, the coupling mechanism 270 (and the receiving arm 210) can be configured so that distal tip 264 of the needle 260 may be moved into the coupling mechanism 270 when the medical device 200 is in the closed configuration and when the medical device 200 is in the open configuration. In some embodiments, the coupling mechanism 270 (and the receiving arm 210) can also be configured so that distal tip 264 of the needle 260 may be moved into the coupling mechanism 270 when the medical device 200 is in a configuration between the closed configuration and the open configuration.

In some embodiments, the coupling mechanism 270 and the needle 260 (or a portion thereof) can be configured to move along a common curve (e.g., arc, line). For example, as shown in FIG. 2D, the distal tip 264 and the coupling mechanism 270 can be configured to move along the arc 60. Accordingly, when the coupling mechanism 270 is moved away from the guide 250 (when the receiving arm 210 is moved away from the clamping arm 220), the distal tip 264 of the needle 260 can still be moved towards the coupling mechanism 270 (along the arc 60) using the sliding mechanism 240 into the cavity 272 of the coupling mechanism 270. Also, when the coupling mechanism 270 is moved toward the guide 250 (when the receiving arm 210 is moved toward the clamping arm 220) the distal tip 264 of the needle 260 can be moved towards the coupling mechanism 270 (along the arc 60) using the sliding mechanism 240 into the cavity 272 of the coupling mechanism 270.

In some embodiments, a centroid and/or axis of the track 230 and/or the needle 260 can be separate from an axis around which the receiving arm 210 and the clamping arm 220 are rotatably coupled. In other words, the receiving arm 210 and the clamping arm 220 can be hingedly coupled at an axis that is separate from a centroid of the track 230 and/or a centroid of the needle 260.

In this embodiment, the clamping arm 220 (and receiving arm 210), the sliding component 240, and the needle 260 can be configured to rotatably move within a plane that is orthogonal to, or substantially orthogonal to, the axis H. The needle 260 can be disposed within the plane. In some embodiments, the radius of curvature of the track 230 and/or of the needle 260 can be between, for example, 2.0 inches (5.08 cm) and 20 inches (50.8 cm) (e.g., 10 inches (25.4 cm), 5 inches (12.7 cm)). In some embodiments, the radius of curvature of the track 230 and/or of the needle 260 can be less than 2.0 inches (5.08 cm), or can be greater than 20 inches (50.8 cm).

As shown in FIG. 2A, the receiving arm 210 includes a coupling mechanism 270 on a distal portion 214 the receiving arm 210. An implant portion 80 configured to be inserted into a body of a patient is coupled to the coupling mechanism 270. In some embodiments, the implant portion 80 can be, for example, a tether coupled to a sling portion of an implant. A zoomed in view (area Y) of the coupling mechanism 270 and the implant portion 80 coupled to the coupling mechanism 270 is shown in FIG. 2C.

FIG. 2C illustrates the coupling mechanism 270 shown in FIG. 2A. As shown in FIG. 2C, the coupling mechanism 270 includes slots 274 into which the implant portion 80 may be inserted. When the implant portion 80 is inserted into the slots 274, a portion 82 of the implant portion 80 spans between the slots 274. In some embodiments, the slots 274 can be sized so that the implant portion 80 may be press fit into one or more of the slots 274. Also as shown in FIG. 2C, the coupling mechanism 270 defines a cavity 272. Although not shown in FIG. 2C, in some embodiments, the coupling mechanism 270 can also be, or can include, a hook, a latch, and/or so forth.

Referring back to FIG. 2A, the coupling mechanism 270 is included in the distal portion 214 of the receiving arm 210. Specifically, the coupling mechanism 270 is included at the end of a curved portion of the receiving arm 210. In some embodiments, coupling mechanism may be included on a different portion of the receiving arm 210 such as a medial portion of the receiving arm 210.

The sliding component 240 (and needle 260) as illustrated in FIG. 2A, is in a stowed configuration. The sliding component 240 can be moved from the stowed configuration (shown in FIG. 2A) to a deployed configuration, shown in FIG. 2E, when the sliding component 240 is moved in direction D1 along the track 230. The sliding component 240 can be moved from the deployed configuration (shown in FIG. 2E) to the stowed configuration (shown in FIG. 2A) by slidably moving the sliding component 240 in direction D2 along the track away from the guide 250.

When in the stowed configuration shown in FIG. 2A, a distal portion 262 of the needle 260 is disposed within (e.g., in a position disposed within) the lumen 252 of the guide 250 or is in a position proximal to (on the right side of) the guide 250. When in the deployed configuration shown in FIG. 2E, the distal portion 262 of the needle 260 is moved outside of (e.g. is moved to position outside of) the lumen 252 of the guide 250 so that the distal portion 262 of the needle 260 is distal to (on the left side of) the guide 250. In this embodiment, the sliding component 240 is slidably moved along the track 230 so that the sliding component 240 is in the deployed configuration shown in FIG. 2E after the medical device 200 is moved to the clamped configuration shown in FIG. 2D.

In some embodiments, when the sliding component 240 is moved to the deployed configuration, the distal tip 264 of the needle 260 will be slidably moved through the lumen 252 of the guide 250 and will pierce a tissue of a patient (for example, if the receiving arm 210 of the medical device 200 is disposed within a body of the patient). For example, the distal tip 264 of the needle 260 can be configured to pierce through a skin tissue, an obturator muscle, and/or another target membrane of the patient and toward the coupling mechanism 270 of the receiving arm 210.

In this embodiment, when the sliding component 240 is in the deployed configuration shown in FIG. 2E, the distal tip 264, and at least a portion of the distal portion 262 of the needle 260 is moved into the cavity 272 of the coupling mechanism 270. The distal tip 264 is moved into the cavity 272 of the coupling mechanism 270 so that a coupling mechanism 266 of the needle 260 may be coupled to (e.g., moved into, engaged with) the implant portion 80. In some embodiments, the coupling mechanism 266 can be, or can include, an opening, a slot, a hook, a latch, a recess, and/or so forth. A zoomed in view of the coupling mechanism 266 of the needle 260 being coupled to the implant portion 80 within the coupling mechanism 270 of the receiving arm 210 is shown in FIG. 2F.

As shown in FIG. 2F, in this embodiment, the coupling mechanism 266 is a slot 267 into which the implant portion 80 is coupled when the distal tip 264, and at least a portion of the distal portion 262, of the needle 260 is moved into the coupling mechanism 270. Specifically, the distal tip 264, the portion of the distal portion 262, of the needle 260 can be moved along direction D1 into the cavity 272 of the coupling mechanism 270 so that the distal tip 264 moves below the implant portion 80. The portion 82 of the implant portion 80 that spans the slots 274 may contact a distal surface 265 of the needle 260 as the distal tip 264 and the portion of the distal portion 262 are moved into the coupling mechanism 270. The portion 82 of the implant portion 80 may be moved along the distal surface 265 until the portion 82 of the implant portion 80 is coupled with (e.g., moved into, engaged with) the coupling mechanism 266 of the needle 260. In some embodiments, the portion 82 of the implant portion 80 may be deflected upward and/or the distal end portion 262 of the needle 260 may be deflected downward as the distal surface 265 of the needle 260 comes into contact with (e.g., contacts, slides along) the portion 82 of the implant portion 80.

During a medical procedure, the coupling mechanism 270 of the receiving arm 210 (and the implant portion 80 coupled thereto) may not be visible to a physician using the medical device 200 when the coupling mechanism 270 of the receiving arm 210 (and the implant portion 80 coupled thereto) are disposed within a body of a patient. Even though the coupling mechanism 270 of the receiving arm 210 (and the implant portion 80 coupled thereto) may not be visible to the physician using the medical device 200 when the sliding component 240 is moved to the deployed configuration, the track 230 and/or the guide 250 may be collectively configured so that the distal tip 264 and the portion of the distal portion 262 may be moved into the coupling mechanism 270 in a desirable fashion. In some embodiments, the needle 260 may be configured (e.g., configured with a stiffness) so that the distal tip 264 of the needle 260, and the portion of the distal portion 262, will be moved into the coupling mechanism 270 without deflecting in an undesirable fashion.

Figure 2G:
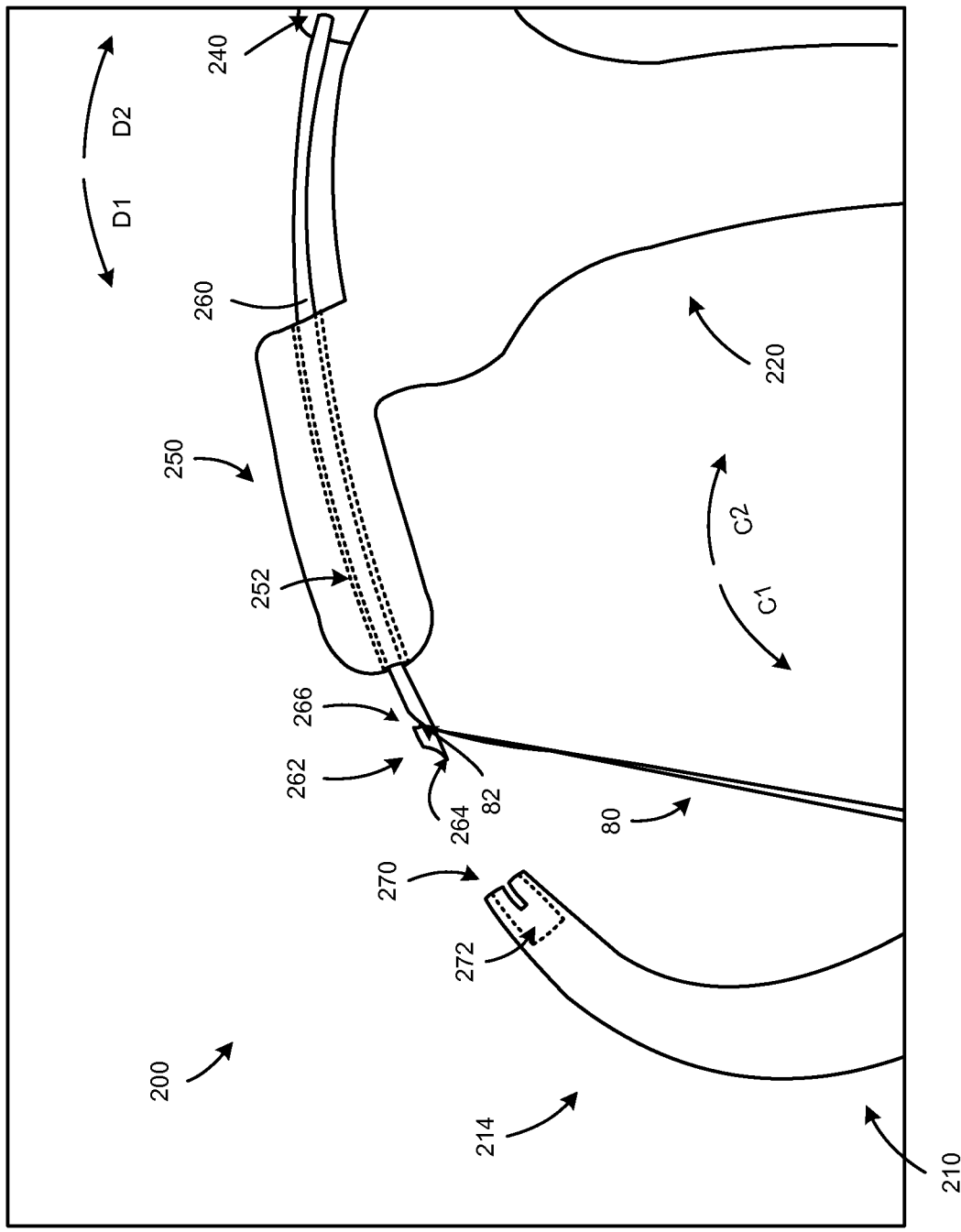
FIG. 2G illustrates an implant portion coupled to a needle of the medical device shown in FIGS. 2A through 2F.

FIG. 2G illustrates the implant portion 80 coupled to the needle 260 of the medical device 200 shown in FIGS. 2A through 2F. As shown in FIG. 2G, the sliding component 240 is in a deployed configuration, but is moved along direction D2 from the deployed configuration shown in FIG. 2E. When the sliding component 240 is moved along direction D2 after the coupling mechanism 266 of the needle 260 is coupled with the implant portion 80, the implant portion 80 is decoupled from the coupling mechanism 270 of the receiving arm 210.

Although not shown in FIG. 2G, the sliding component 240 may be moved along direction D2 until the sliding component 240 is in a stowed configuration. In such embodiments, at least a portion of the implant portion 80 may be moved into the lumen 252 of the guide 250 while coupled to the coupling mechanism 266 of the needle 260. In some embodiments, at least a portion of the implant portion 80 may be moved until the portion of the implant portion 80 is disposed outside of the lumen 252 on a proximal side (e.g., the right side) of the guide 250 while coupled to the coupling mechanism 266 of the needle 260. In some embodiments, as the sliding component 240 is moved along direction D2 at least a portion of the implant portion 80 may be moved outside of the body of the patient by the needle 260 and the sliding component 240.

Although not shown, in some embodiments, as the sliding component 240 is moved along direction D2 at least a portion of the implant portion 80 may be moved to a desirable position with the body of the patient by the needle 260 and the sliding component 240. In such embodiments, the portion of the implant portion 80 can be released from the needle 260 (using an actuating mechanism) so that the implant portion 80 may be placed within the body of the patient.

In some embodiments, the needle 260 can define a lumen that is configured to convey fluids to and/or from a body of a patient. As shown in FIG. 2A, 2D, and 2E the sliding component 240 of the medical device 200 has an opening 242 configured to be coupled to a fluid delivery device. The opening 242 can be in fluid communication with the lumen of the needle 260 so that a fluid can be delivered from the fluid delivery device via the opening 242 and into the lumen of the needle 260. More details related to fluid delivery via the medical device 200 are described in connection with FIG. 4.

Because the guide 250 can function as a support for the needle 260, the needle 260 can have a cross-sectional area (along a plane orthogonal (or approximately orthogonal) to a longitudinal axis of the needle 260) that is smaller than would otherwise be permissible without the guide 250. In other words, the needle 260 can be relatively thin (e.g., can have a relatively small diameter) because only a relatively short portion of the needle 260 may project from the guide 250 when the sliding component 240 is in the deployed configuration. In some embodiments, the diameter of the needle 260 can be less than 3 millimeters (mm). For example, in some embodiments, the needle 260 can have a diameter of approximately 2.5 mm. In some embodiments, the needle 260 can have a diameter less than 2.5 mm or a diameter greater than 2.5 mm. Also, because the guide 250 can function as a support for the needle 260, the needle 260 can have a curvature that is greater than (e.g., has a smaller radius of curvature) would otherwise be permissible without the guide 250. In some embodiments, the coupling mechanism 270 of the receiving arm 210 can be moved so that the coupling mechanism 270 is contacting, or is relatively close to (e.g., less than 2 mm, less than 2 cm), a tissue through which at least a portion of the needle 260 is to pierce (on the opposite side).

Figure 3:
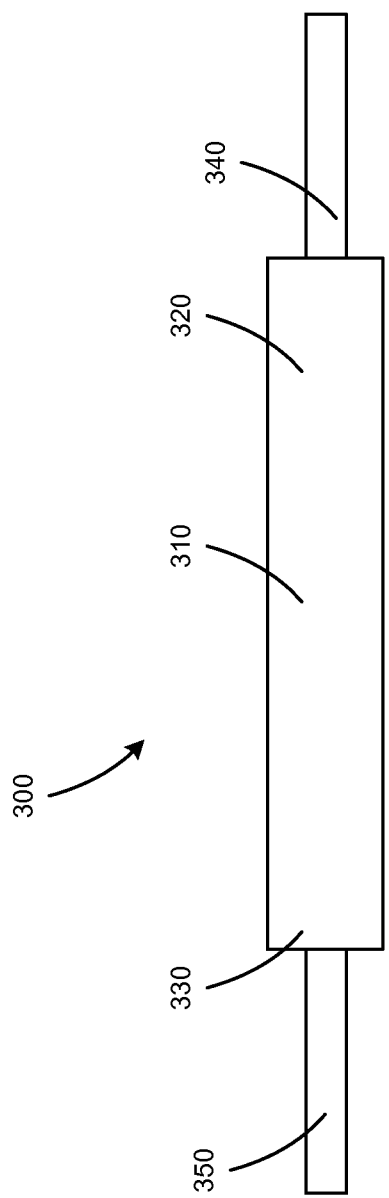
FIG. 3 is a schematic diagram of an implant, according to an embodiment.

The medical devices described herein (e.g., the medical devices 100 and 200 shown in FIGS. 1 and 2) may be used to insert an implant into a pelvic region of a patient. For example, an implant 300 as illustrated in FIG. 3 may be implanted into a pelvic region of a patient using the medical devices. The implant 300 shown in FIG. 3 is a sling and includes a support portion 310, end portions 320 and 330, and association members 340 and 350. In some embodiments, the association members 340, 350 can be tethers. The support potion 310 can be configured to be placed proximate a portion of the body of the patient and can be configured to provide support to the portion of the body. The end portions 330 and 340 can be configured to be placed into and coupled to bodily tissue to anchor the implant 300 within the body of the patient. The association members 340 and 350 can be configured to associate the implant 300 to the medical devices during an implantation procedure.

In some embodiments, the implant 300 may be formed of any biocompatible material. In some embodiments, the implant 300 can be formed of a mesh material. For example, the implant 300 may be formed of Advantage® mesh or the Polyform™ synthetic mesh, both as produced and/or sold by Boston Scientific Corporation. In some embodiments, the implant 300 may be formed of a polymer material. In some embodiments, the material of the implant 300 allows for tissue in-growth to secure the implant 300 to the bodily tissue of the patient.

In some embodiments, the implant 300 can include tangs to help retain the implant 300 in place within the body of the patient. In such embodiments, the tang or tangs can be configured to engage the bodily tissue surrounding the implant 300 help retain the implant 300 in place within the body of the patient. The terms "tanged" or "tangs" as used herein mean roughened or jagged edges or areas, such as can result from cutting a woven or knit mesh material.

Figure 4A:
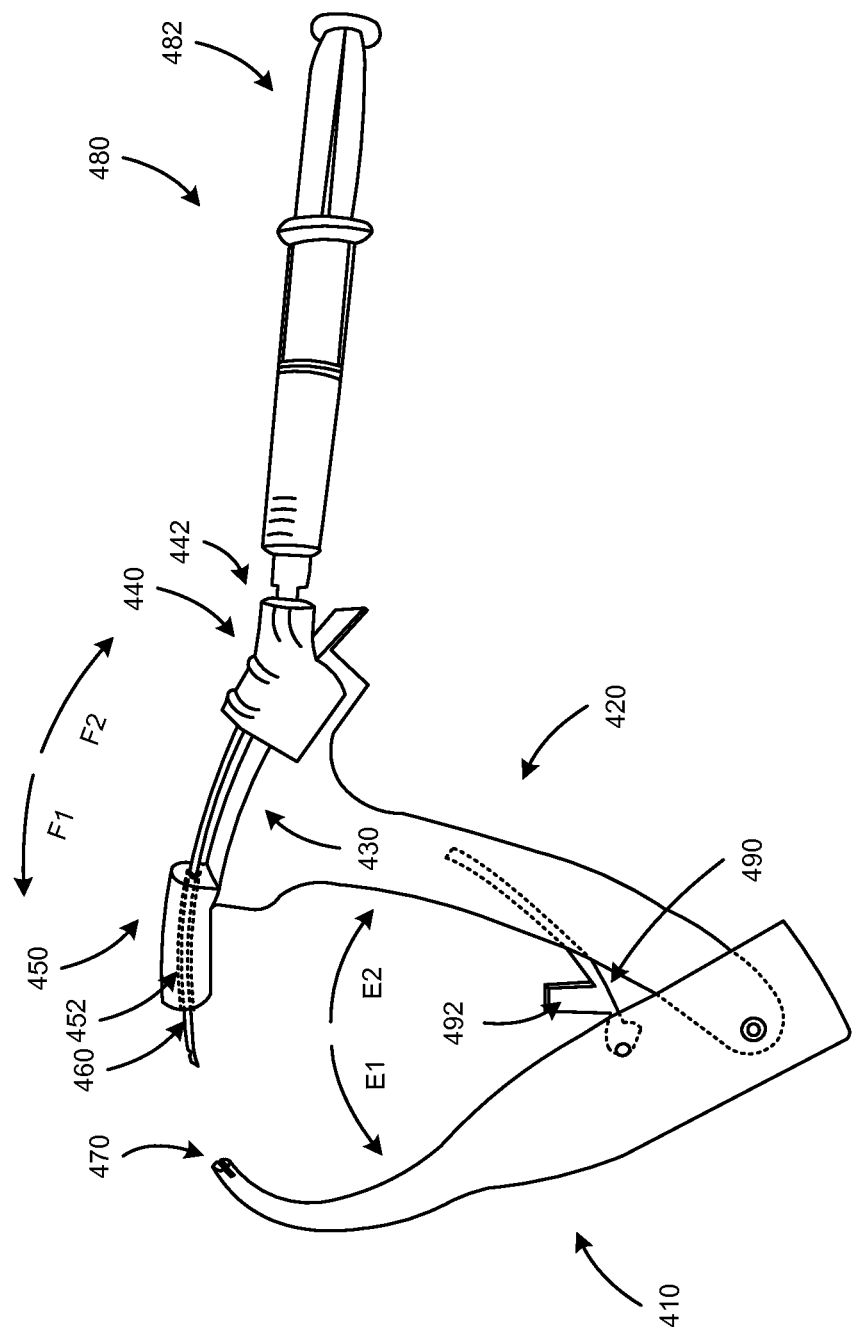
FIG. 4A illustrates a medical device coupled to a syringe according to an embodiment.

FIG. 4A illustrates a medical device 400 coupled to a syringe 480, according to an embodiment. The medical device 400 is configured to be used as an insertion tool or delivery tool to implant or insert a bodily implant (not shown) into a body of a patient (e.g., using an outside-in approach via a vaginal incision in the body of the patient).

As shown in FIG. 4A, the medical device 400 has a receiving arm 410 coupled (e.g., rotatably coupled, hingedly coupled) to a clamping arm 420. The clamping arm 420 can be moved (e.g., rotatably moved) with respect to the receiving arm 410 in a direction E1 and/or direction E2. The medical device 400 shown in FIG. 4A is in a clamped configuration, in some embodiments, the medical device 400 can also be moved to an open configuration. A sliding component 440 may be slidably moved along a track 430 in direction F1 (towards a coupling mechanism 470) and/or direction F2 (away from the coupling mechanism 470). The sliding component 440 is shown in a deployed configuration in FIG. 4A, and, in some embodiments, the sliding component 440 may also be moved to a stowed configuration. The sliding component 440 is coupled to (or includes) a needle 460 that is configured to slidably move within a lumen 452 of the guide 450.

In the embodiment shown in FIG. 4A the needle 460 of the medical device 400 is configured to convey a fluid. The needle 460 can define a lumen that is configured to convey fluids to and/or from a body of a patient. As shown in FIG. 4A, the sliding component 440 has a proximal portion 442 that is coupled to the syringe 480. The syringe 480 is configured to deliver a fluid to and/or draw a fluid from the needle 460. In some embodiments, the syringe 480 is a 40 cc syringe. In other embodiments, the syringe 480 is larger or smaller than 40 cc. In some embodiments, a device other than a syringe may be used to move a liquid through the needle 460.

Although not shown in FIG. 4A, a tube, tether, or other device configured to convey a fluid can be disposed between the sliding component 440 and the syringe 480. In other words, the syringe 480 can be configured to deliver a fluid via a tube to the sliding component 440. In such embodiments, the sliding mechanism 440 can be operated by a first person (e.g., a first physician) and the syringe 480 can be operated by a second person (e.g., a second physician).

In some embodiments, the syringe 480 may be coupled to the sliding component 440 in a relatively rigid fashion so that the syringe 480 may be used by a physician to move the sliding component 440. In other words, the medical device 400 may be configured so that a physician can slidably move the sliding component 440 along the track 430 by applying a force (e.g., a pulling force, a pushing force) to the syringe 480. In some embodiments, the medical device 400 may be configured so that a physician can push and/or pull a plunger 482 of the syringe 480 (while moving the sliding component 440) to deliver and/or withdraw, respectively, a fluid from the lumen of the needle 460. Thus, a fluid may be delivered and/or withdrawn via the needle 460 while the sliding component 440 is in, or moving to, the stowed configuration and/or is in, or moving to, the deployed configuration. In some embodiments, the fluid may be delivered and/or withdrawn via the needle 460 while the medical device 400 is in, or moving to, the clamped configuration and/or is in, or moving to, the open configuration.

In some embodiments, for example, a lumen defined by the needle 460 may be used to deliver medication or anesthesia to the body of the patient during the procedure to place an implant within the body of the patient. In some embodiments, the lumen may be used to help hydro-dissect the bodily tissue during an implantation procedure. The lumen defined by the needle 460 may be of any shape or size. For example, the cross-sectional shape (or outer profile) of the lumen may be circular, square, or rectangular.

As shown in FIG. 4A, the medical device 400 has a locking mechanism 490 configured to lockably couple the clamping arm 420 with respect to the receiving arm 410. In other words, locking mechanism 490 can be used to releasably lock the medical device 400 in one or more open configurations and/or one or more clamped configurations. Although not shown in FIG. 4A, the locking mechanism 490 can have one or more protrusions (e.g., teeth, latches) (not shown) that can be used to be coupled to (e.g., contact, catch on) one or more protrusions (e.g., teeth, gear teeth) (not shown) disposed within the clamping arm 420. The protrusions, when coupled to the protrusion(s), can releasably lock a position of the receiving arm 410 with respect to a position of the clamping arm 420.

As shown in FIG. 4A, at least a first portion of the locking mechanism 490 is disposed within the receiving arm 410 and at least a second portion of locking mechanism 490 is disposed within the clamping arm 420. In some embodiments, at least a portion of locking mechanism 490 may not be disposed inside of the receiving arm 410 and/or the clamping arm 420.

As shown in FIG. 4A, the locking mechanism 490 has a control lever 492 (when pushed and/or pulled by a physician) that can be used to trigger the locking mechanism 490 to releasably lock the medical device 400 in one or more open configurations and/or one or more clamped configurations. The control lever 492 (when pushed and/or pulled by a physician) can also be configured to release the medical device 400 from one or more releasably locked configurations.

Although not shown in FIG. 4A, in some embodiments, movement of the receiving arm 410 can be limited with respect to the clamping arm 420. For example, movement of the receiving arm 410 can be limited so that the receiving arm 410, or a portion thereof (e.g., the coupling mechanism 470), may not come in contact with the clamping arm 420. In some embodiments, the movement of the receiving arm 410 can be limited with respect to the clamping arm 420 by the locking mechanism 490 and/or a stop (not shown) disposed between the receiving arm 410 and the clamping arm 420.

Figure 4B:
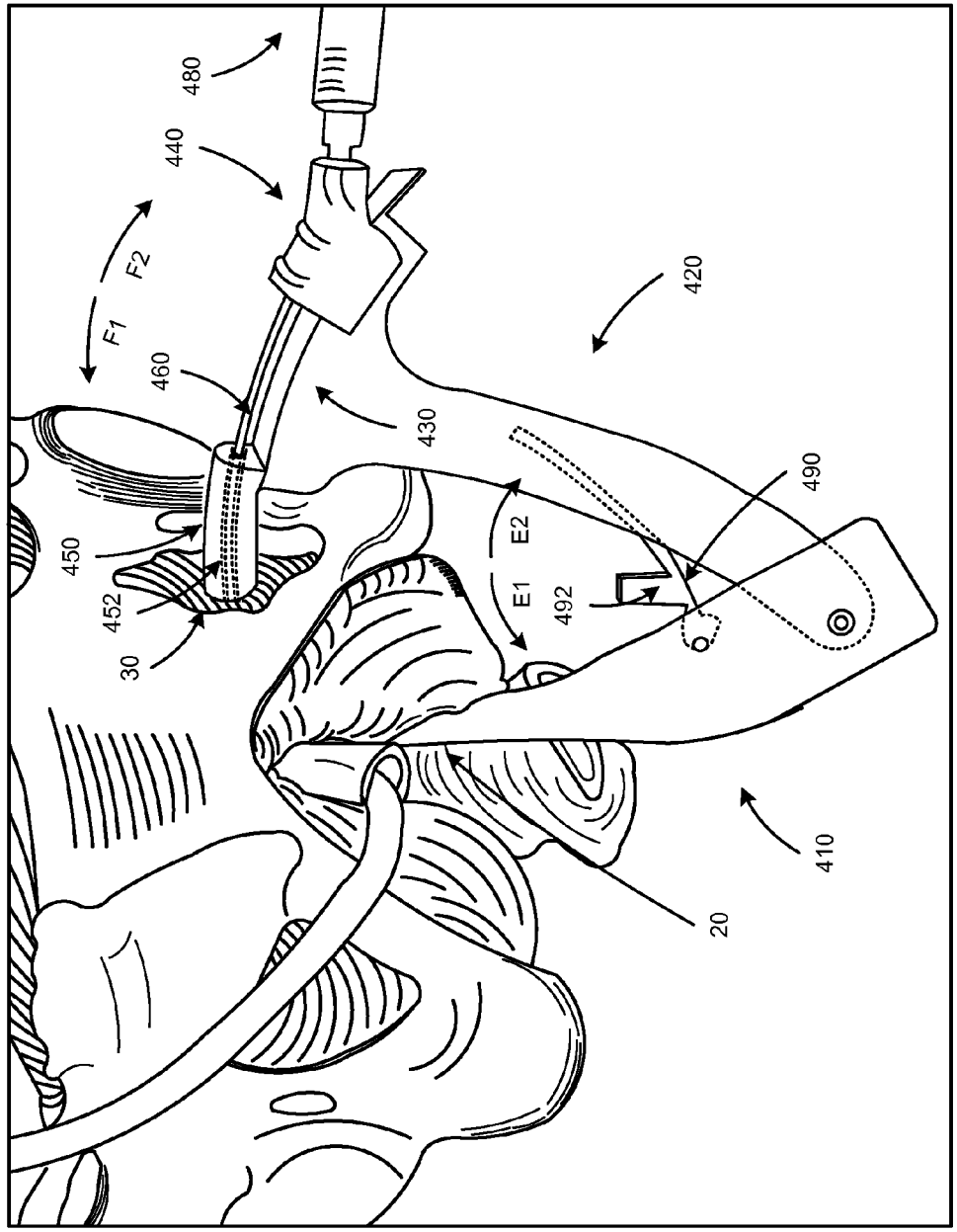
FIG. 4B schematically illustrates the medical device shown in FIG. 4A in use with a body of a patient.

FIG. 4B schematically illustrates the medical device 400 shown in FIG. 4A in use with a body of a patient. As shown in FIG. 4B, at least a portion of the receiving arm 410 of the medical device 400 is disposed within a vaginal region 20 of a body of a patient. Also as shown in FIG. 4B, the guide 450 of the clamping arm 420 is in relatively close proximity to an obturator foramens 30 of the patient. The sliding component 440 is in a deployed configuration so that at least a portion of the needle 460 pierces a tissue of the patient and is disposed within the body of the patient.

Figure 5:
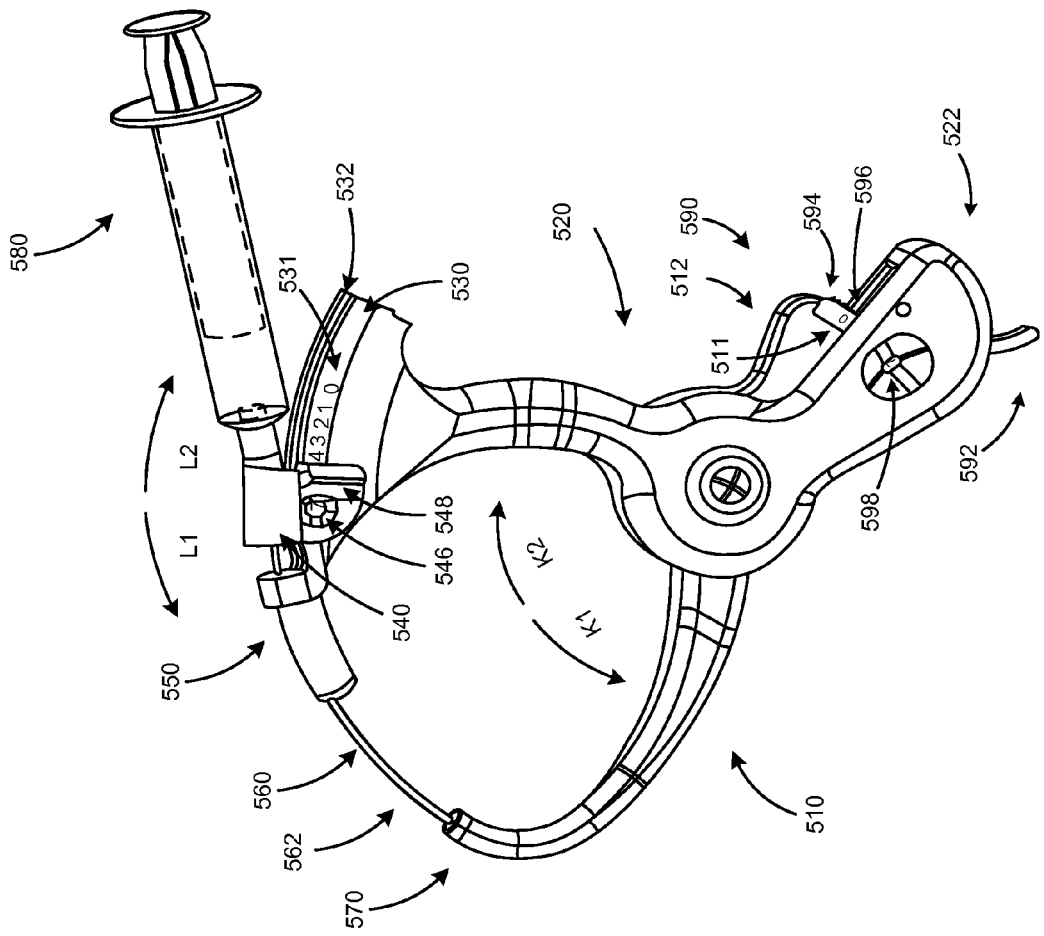
FIG. 5 illustrates another medical device according to an embodiment.

FIG. 5 illustrates another medical device 500, according to an embodiment. The medical device 500 is configured to be used as an insertion tool or delivery tool to implant or insert a bodily implant (not shown) into a body of a patient (e.g., using an outside-in approach via a vaginal incision in the body of the patient).

As shown in FIG. 5, the medical device 500 has a receiving arm 510 coupled (e.g., hingedly coupled, rotatably coupled) to a clamping arm 520. The clamping arm 520 can be moved (e.g., rotatably moved) with respect to the receiving arm 510 in a direction K1 and/or a direction K2. The medical device 500 shown in FIG. 5 is in a clamped configuration, in some embodiments, the medical device 500 can also be moved to an open configuration. In this embodiment, the receiving arm 510 of the medical device 500 has a medial portion hingedly coupled to a medial portion of the clamping arm 520 of the medical device 500.

As shown in FIG. 5, a sliding component 540 may be slidably moved along a track 530 in direction L1 (towards a coupling mechanism 570) and/or direction L2 (away from the coupling mechanism 570). As shown in FIG. 5, the track 530 has a groove 532 along which sliding component 540 slidably moves. Although not shown in FIG. 5, in some embodiments, the sliding component has a protrusion configured to slidably move within the groove 532. Also, as shown in FIG. 5, the sliding component 540 includes a tab 548 (also can be referred to as a protrusion) that can be used to push and/or pull the sliding component 540.

The sliding component 540 is shown in a deployed configuration in FIG. 5. In some embodiments, the sliding component 540 may also be moved to a stowed configuration (where a distal portion 562 of the needle 560 is disposed within a lumen 552 of a guide 550). The sliding component 540 is coupled to (or includes) a needle 560 that is configured to slidably move within the lumen 552 of the guide 550.

In the embodiment shown in FIG. 5 the needle 560 of the medical device 500 is configured to convey a fluid. The needle 560 can define a lumen that is configured to convey fluids to and/or from a body of a patient. As shown in FIG. 5, the sliding component 540 is coupled to a syringe 580. The syringe 580 is configured to deliver a fluid to and/or draw a fluid from the needle 560.

As shown in FIG. 5, the medical device 500 has a locking mechanism 590 configured to lockably couple the clamping arm 520 with respect to the receiving arm 510. In this embodiment, the locking mechanism 590 can be referred to as a ratchet mechanism. The locking mechanism 590 can be used to releasably lock the medical device 500 in one or more open configurations and/or one or more clamped configurations.

The locking mechanism 590 has protrusions 594 (e.g., teeth) that can be configured to be coupled to (e.g., contact, catch on) protrusions 596 (not shown in FIG. 5) (e.g., teeth) disposed within the clamping arm 520 (and facing the protrusions 594). The protrusions 594, when coupled to (e.g., contacted with) the protrusions 596, can lock a position of the receiving arm 510 with respect to a position of the clamping arm 520. The coupling of one or more of protrusions 594 to one or more of the protrusions 596 can be released using lever 592.

In some embodiments, the locking mechanism 590 can be biased so that the position of the receiving arm 510 is lockably coupled (e.g., automatically lockably coupled) with respect to a position of the clamping arm 520 using the locking mechanism when the receiving arm 510 is moved with respect to the clamping arm 520. In other words, the protrusions 594 and the protrusions 596 can be biased (e.g., biased using a spring) to contact one another as the clamping arm 520 and the receiving arm 510 are moved with respect to one another. In such embodiments, lockable coupling of the position of the receiving arm 510 with respect to the position of the clamping arm 520 can be released using the lever 592. In some embodiments, the locking mechanism 590 can be biased so that the position of the receiving arm 510 is lockably coupled with respect to a position of the clamping arm 520 in response to the lever being actuated. In other words, the locking mechanism 590 can be biased to an unlocked configuration. In such embodiments, the protrusions 594 and the protrusions 596 may not be biased (e.g., biased using a spring) away from one another and may not come into contact until activated using the lever 592.

As shown in FIG. 5, the locking mechanism 590 is defined by at least a portion (i.e., a proximal portion 512) of the receiving arm 510, which is disposed within at least a portion (i.e., a proximal portion 522) of the clamping arm 520. In some embodiments, at least a portion of locking mechanism 590 may not be disposed inside of the receiving arm 510 and/or the clamping arm 520. In this embodiment, at least a portion of the proximal portion 512 of the receiving arm 510 and at least a portion of the proximal portion 522 of the clamping arm 520 collectively define a handle portion of the medical device 500.

As shown in FIG. 5, the proximal portion 522 of the clamping arm 520 has a window 598 through which indicators 511 (e.g., numbers, marks, detents) included in the proximal portion 512 of the receiving arm 510 may be seen. The indicators 511 and the window 598 can be configured so that one or more of the indicators 511 visible through the window 598 can be an indicator of, for example, a distance between at least a portion of the receiving arm 510 (e.g., the coupling mechanism 570) and at least a portion of the clamping arm 520 (e.g., the track 530, a distal portion of the guide 550). In some embodiments, one or more of the indicators 511 can be an indicator of a relative positions (when the medical device 500 is in an open configuration and/or a clamped configuration) of at least a portion of the receiving arm 510 and at least a portion of the clamping arm 520.

As shown in FIG. 5, the sliding mechanism 540 has a window 546 through which indicators 531 (e.g., numbers, marks, detents) associated with (e.g., along) the track 530 may be seen. In some embodiments, the window 546 and the indicators 531 can collectively define an indicator mechanism. The indicators 531 and the window 546 can be configured so that one or more of the indicators 531 visible through the window 546 can be an indicator of, for example, a distance between at least a portion of the sliding component 540 and/or needle 560 (e.g., the distal portion 562 of the needle 560) and at least a portion of the receiving arm 510 (e.g., the coupling mechanism 570). In other words, one or more of the indicators 531 can be an indicator of a relative position (when in a stowed configuration and/or a deployed configuration) between at least a portion of the sliding component 540 and/or needle 560 (e.g., the distal portion 562 of the needle 560) and at least a portion of the receiving arm 510 (e.g., the coupling mechanism 570).

In some embodiments, the indicators 531 associated with (e.g., along) the track 530 can be correlated with the indicators 511 included on the proximal portion 512 of the receiving arm 510 so that one or more of the indicators 531 can be used to determine when at least a portion of the distal portion 562 of the needle 560 is disposed within the coupling mechanism 570 and/or has contacted a portion of an implant coupled with the coupling mechanism 570. For example, when the receiving arm 510 can be moved within respect to a position of the clamping arm 520 in a clamped configuration of medical device 500 until an indicator from the indicators 511 is visible through the window 598. The medical device 500 can be configured so that at least a portion (e.g., a distal tip) of the distal portion 562 of the needle 560 will be disposed within the coupling mechanism 570 when the sliding component 540 is moved until an indicator from the indicators 531 that is visible through the window 546 matches the indicator from the indicators 511. In some embodiments, the window 598 and the indicators 511 can collectively define an indicator mechanism.

In some embodiments, medical device 500 can include one or more electronic indicators (e.g., light emitting diode (LED) indicators coupled to electronic contacts and a power supply, liquid crystal display indicators triggered by a microprocessor). For example, the medical device 500 can include an electronic indicator configured to indicate a position of at least a portion of the receiving arm 510 (e.g., the coupling mechanism 570) with respect to at least a portion of the clamping arm 520 (e.g., the track 530, a distal portion of the guide 550). In some embodiments, the medical device 500 can include an electronic indicator configured to indicate a relative position between at least a portion of the sliding component 540 and/or needle 560 (e.g., the distal portion 562 of the needle 560) and at least a portion of the receiving arm 510 (e.g., the coupling mechanism 570).

Figure 6:
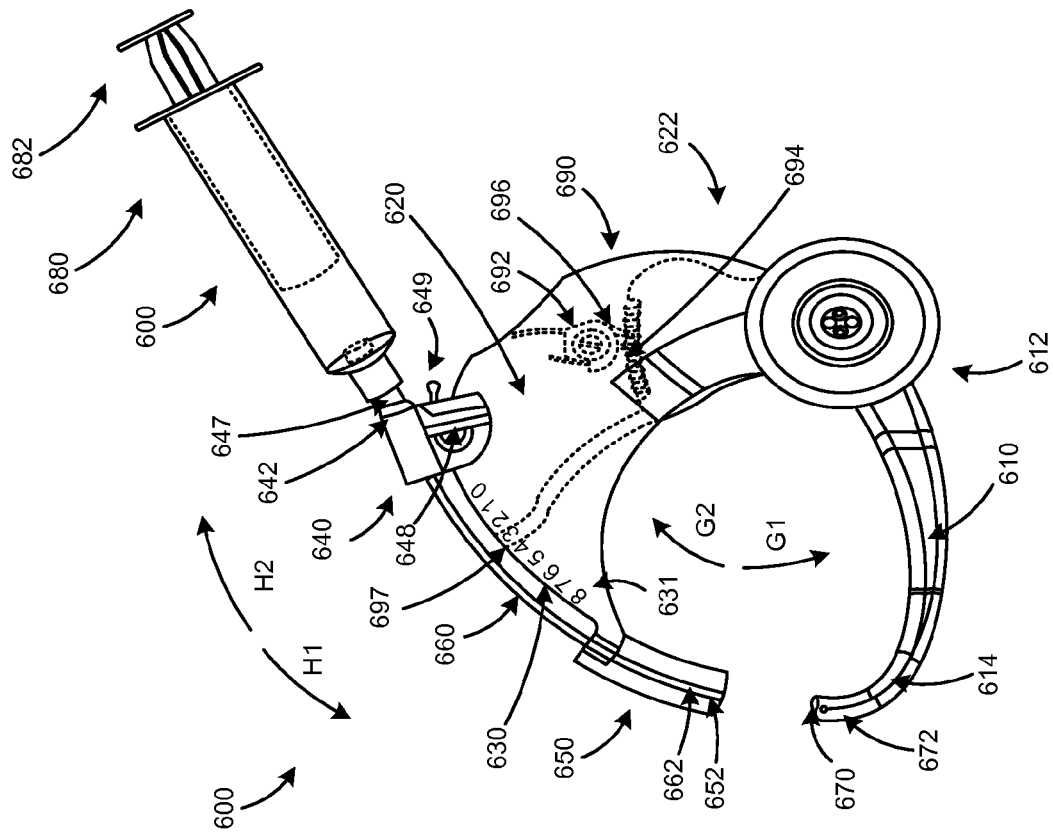
FIG. 6 illustrates yet another medical device according to an embodiment.

FIG. 6 illustrates yet another medical device 600 according to an embodiment. The medical device 600 is configured to be used as an insertion tool or delivery tool to implant or insert a bodily implant (not shown) into a body of a patient. As shown in FIG. 6, the medical device 600 has a receiving arm 610 coupled (e.g., hingedly coupled) to a clamping arm 620. The clamping arm 620 can be moved (e.g., rotatably moved) with respect to the receiving arm 610 in a direction G1 and/or a direction G2. The medical device 600 shown in FIG. 6 is in a clamped configuration, in some embodiments, the medical device 600 can also be moved to an open configuration. In this embodiment, the receiving arm 610 of the medical device 600 has a proximal portion 612 hingedly coupled to a proximal portion 622 of the clamping arm 620 of the medical device 600.

As shown in FIG. 6, a sliding component 640 may be slidably moved along a track 630 in direction H1 (towards a coupling mechanism 670) and/or direction H2 (away from the coupling mechanism 670). In this embodiment, the coupling mechanism 670 defines a cavity 672. As shown in FIG. 6, the track 630 has a groove 632 along which sliding component 640 slidably moves.

The sliding component 640 is shown in a stowed configuration in FIG. 6 (where a distal portion 662 of a needle 660 is disposed within a lumen 652 of a guide 650). In some embodiments, the sliding component 640 may also be moved to a deployed configuration (not shown). The needle 660 is coupled to the sliding component 640 and is configured to slidably move within the lumen 652 of the guide 650.

As shown in FIG. 6, the sliding component 640 includes a locking mechanism 647 configured to releasably lock the sliding component 640 in a position along the track 630. In some embodiments, the sliding component 640 can be releasably locked in any position along the track 630 using a lever 649 (e.g., a protrusion, a tab). For example, the sliding component 640 can be releasably locked in the stowed configuration shown in FIG. 6.

In some embodiments, the locking mechanism 647 can be biased so that the sliding component 640 may not be moved along the track 630 unless the lever 649 is actuated. In other words, the locking mechanism 647 can be configured so that the lever 649 can be actuated to release the locking mechanism so that the sliding component 640 may be slidably moved along the track 630. In some embodiments, the locking mechanism 647 can be biased so that the sliding component 640 may not be locked into a position along the track 630 until actuated using the lever 649. In other words, the locking mechanism 647 can be configured so that the lever 649 can be actuated to lock the sliding component 640 along the track 630.

In the embodiment shown in FIG. 6 the needle 660 of the medical device 600 is configured to convey a fluid. The needle 660 can define a lumen that is configured to convey fluids to and/or from a body of a patient. As shown in FIG. 6, the sliding component 640 is coupled at 642 to a syringe 680 that has a plunger 682. The syringe 680 is configured to deliver a fluid to and/or draw a fluid from the needle 660.

As shown in FIG. 6, the medical device 600 has a locking mechanism 690 configured to lockably couple the clamping arm 620 with respect to the receiving arm 610. In this embodiment, the locking mechanism 690 can be referred to as a ratchet mechanism. The locking mechanism 690 can be used to releasably lock the medical device 600 in one or more open configurations and/or one or more clamped configurations. As shown in FIG. 6, the sliding component 640 includes a tab 648 (also can be referred to as a protrusion) that can be used to push and/or pull the sliding component 640.

The locking mechanism 690 has protrusions 694 (e.g., teeth) that can be configured to be coupled to (e.g., contact, catch on) a protrusion 696 disposed within the clamping arm 620 (and facing the protrusions 694). The protrusions 694, when coupled to (e.g., contacted with) the protrusion 696, can lock a position of the receiving arm 610 with respect to a position of the clamping arm 620. The coupling of one or more of the protrusions 694 to the protrusion 696 can be released using a rotatable lever 692. In some embodiments, the locking mechanism 690 can be biased (via the rotatable lever 692) towards a locked configuration (e.g., being lockably coupled), or biased to an unlocked configuration.

As shown in FIG. 6, the medical device 600 includes an indicator member 697 (coupled to the locking mechanism 690) configured to align with one or more of the indicators 631 associated with (aligned along) the track 630. In some embodiments, the indicator member 697 and the indicators 631 can collectively define an indicator mechanism. In some embodiments, the indicator member 697, when aligned with one or more of the indicators 631, can indicate, for example, a distance between at least a portion of the receiving arm 610 (e.g., the coupling mechanism 670) and at least a portion of the clamping arm 620 (e.g., the track 630, a distal portion of the guide 650). In other words, one or more of the indicators 631 (when pointed to by the indicator member 697) can be an indicator of a relative positions (when the medical device 600 is in an open configuration and/or a clamped configuration) of at least a portion of the receiving arm 610 and at least a portion of the clamping arm 620.

In some embodiments, the indicator member 697 can also be configured to limit movement of the sliding component 640. For example, as shown in FIG. 6, the indicator member 697 can be configured to prevent (e.g., configured to prevent as a safety stop) the sliding component 640 from movement to a position beyond the indicator member 697. The sliding component 640 can have a protrusion (e.g., a tab) (not shown) that limits (e.g., stops) the movement of the sliding component 640 when the protrusion comes into contact with the indicator member 697. In some embodiments, the indicator member 697 may not function as a safety stop. In some embodiments, the medical device 600 (e.g., the sliding component 640, the track 630) can have a safety stop that does not function as an indicator. In some embodiments, a safety stop can be configured to limit the movement of the sliding component 640 so that the needle 660 may not be moved into a body of a patient in an undesirable fashion (e.g., beyond a specified point within the body of the patient).

In some embodiments, the indicator member 697, when aligned with one or more of the indicators 631, can indicate, for example, a target position of the sliding component 640 along the track 630. The target position can be a position at which at least a portion of the needle 660 is, for example, moved into or near the cavity 672 of the coupling mechanism 670 so that the needle 660 is coupled to at least a portion of an implant coupled to the coupling mechanism 670. In some embodiments, the target position can be a position at which at least a portion of the needle 660 comes into contact with at least a portion of an implant coupled to the coupling mechanism 670.

In some embodiments, the indicator member 697 can be configured so that the distal portion 662 of the needle 660 will precisely move into the cavity 672 of the coupling mechanism 670 of the receiving arm 610. For example, the receiving arm 610 can be moved towards the clamping arm 620 so that a distal end (a front portion) of the guide 650 is a distance from the coupling mechanism 670. The indicator member 697 can be configured to limit the movement of the sliding component so that the portion of the needle 660 that is extended from (deployed from) the distal end of the guide 650 has a length that is approximately equal to, slightly greater than, or equal to the distance.

Figure 7A:
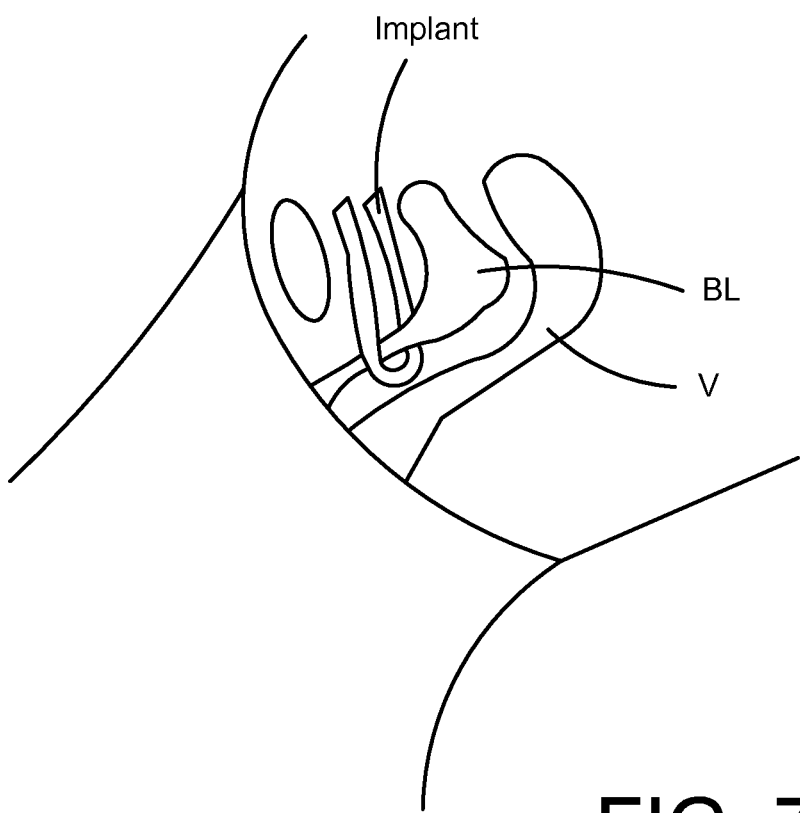
FIGS. 7A, 7B, and 7C schematically illustrate implants disposed within a body of a patient.

In some embodiments, as schematically illustrated in FIG. 7A, an implant (such as the implant 300 shown in FIG. 3) can be positioned, at least in part, by the medical devices described herein between a portion of a vagina V of a patient and a portion of a bladder BL of the patient such that the implant provides support to the bladder BL of the patient.

Figure 7B:
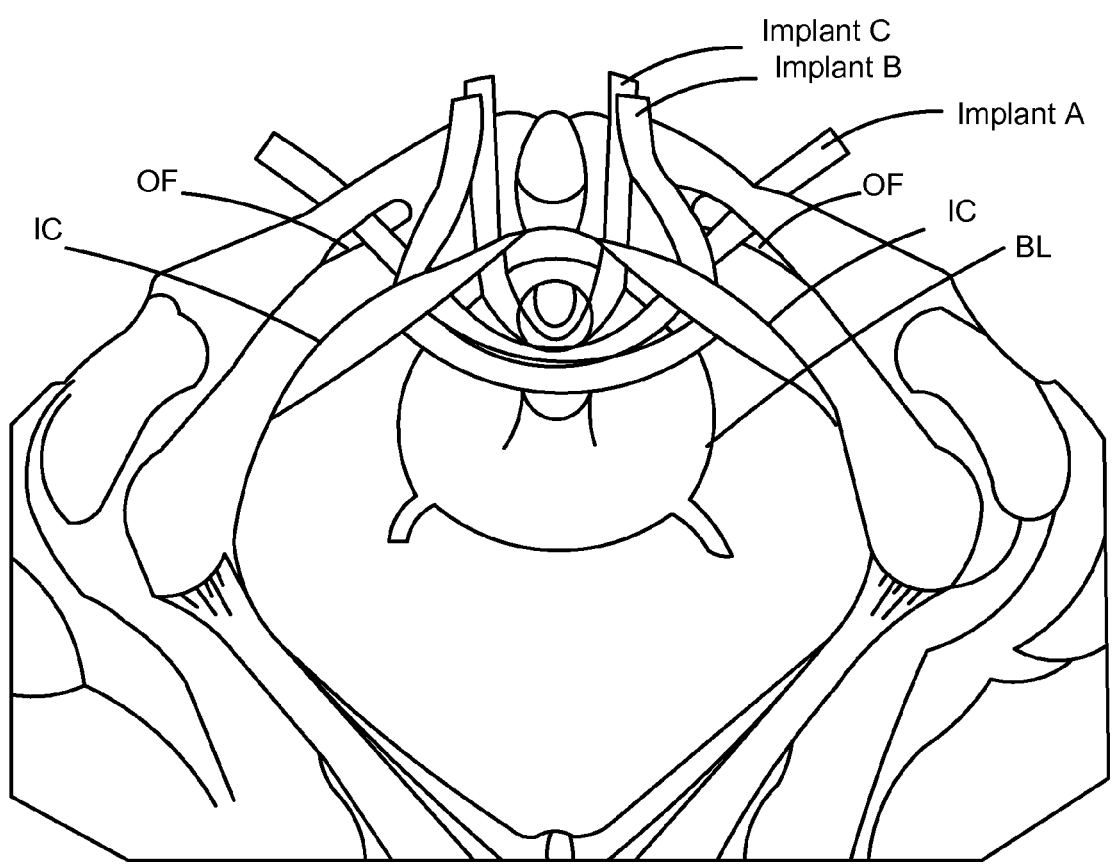

As illustrated in FIG. 7B, an implant (such as the implant 300 shown in FIG. 3) may be positioned, at least in part, by the medical devices described herein at different locations within the body of the patient. For example, as illustrated in FIG. 7B, implant A may be placed within the body of the patient such that the implant A extends through the obturator foramens OF of the patient. Alternatively, as illustrated, the implant B may extend between the midline incision, Ischiocavernosus muscle IC and in front of the pubic bone (prepubic approach). Alternatively, as illustrated, implant C may be disposed within the body of the patient in a "V" shape. Although not shown, in some embodiments, the implant B may extend between the ATFP (arcus tendineus facia pelvis) and the obturators of the patient.

Figure 7C:
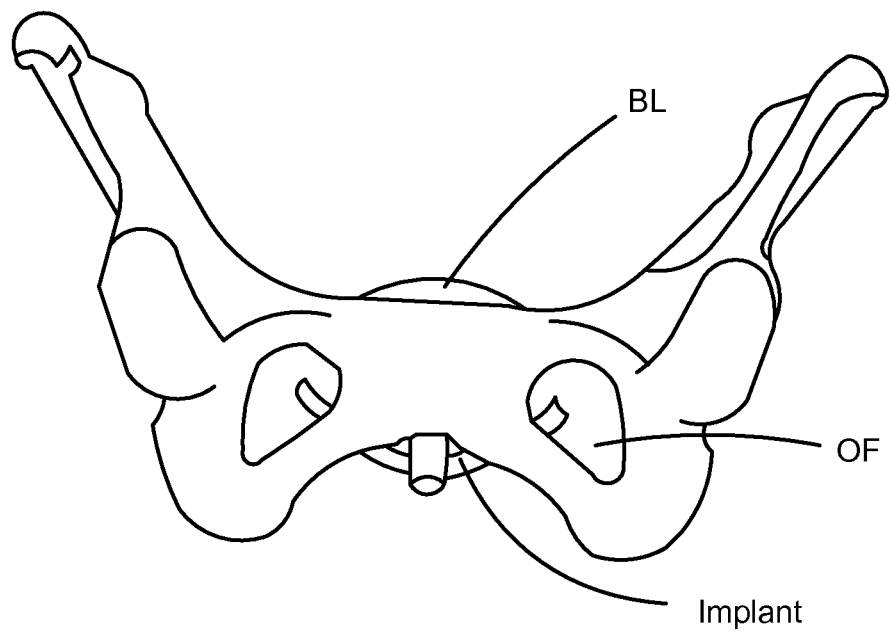

As illustrated in FIG. 7C, an implant (such as the implant 300 shown in FIG. 3) may be placed, at least in part, by the medical devices described herein such that it extends toward the obturator foramens OF of the patient, but does not extend through the obturator foramens OF. For example, the implant may be disposed within or coupled to muscles disposed proximate the obturator foramens OF. In some embodiments, the implant may be decoupled from an end of a needle (after being retrieved from a coupling mechanism) of the medical device after being placed within a desirable location within the body of the patient using a decoupling mechanism (e.g., a latch mechanism, a decoupling mechanism at an end of the needle member) controlled using, for example, a lever, trigger, and/or so forth. In some embodiments, the medical devices described herein may be used to deliver an implant to the pelvic region of the patient via a retropubic (below) or a suprapubic (above) approach.

Figure 8:
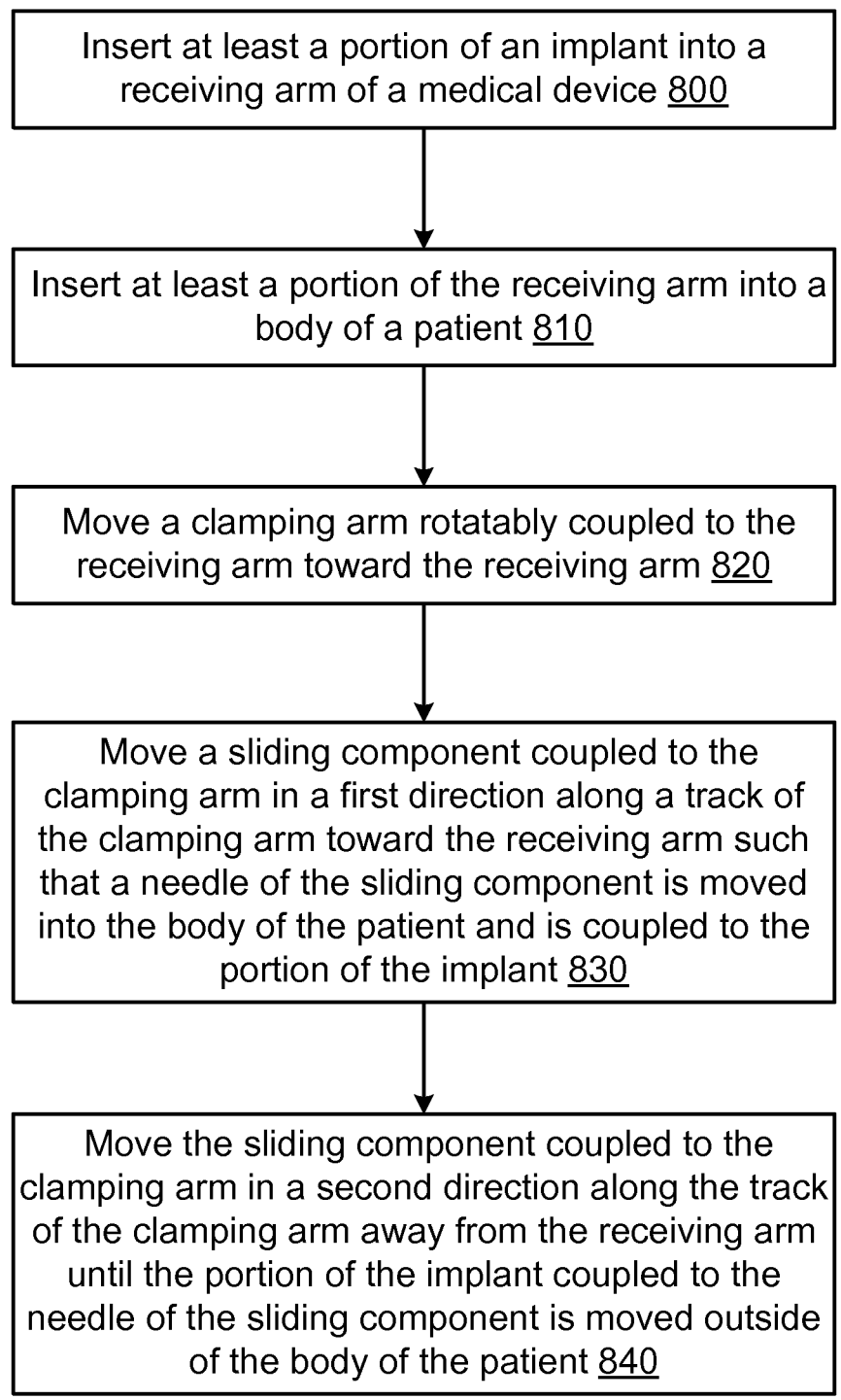
FIG. 8 is a flow diagram that illustrates a method for using a medical device.

FIG. 8 is a flow diagram that illustrates a method for using a medical device. In some embodiments, the medical device can be similar to, or the same as, the medical devices (e.g., medical device 100 shown in FIG. 1, medical device 200 shown in FIG. 2A) described above.

At least a portion of an implant is inserted into a receiving arm of a medical device (block 800). In some embodiments, the portion of the implant can be, for example, a tether or suture of the implant. In some embodiments, the portion of the implant can be inserted into a coupling mechanism of a receiving arm.

At least a portion of the receiving arm is inserted into a body of a patient (block 810). In some embodiments, the receiving arm can be inserted into a vaginal region of a body of a patient or a rectal region of a body of a patient. The receiving arm can be inserted after the portion of the implant is coupled to the coupling mechanism.

A clamping arm rotatably coupled to the receiving arm moved toward the receiving arm (block 820). In some embodiments, the clamping arm can be hingedly coupled to the receiving arm of the medical device. The clamping arm can be moved towards the receiving arm until a guide of the clamping arm is compressed against a skin tissue of the patient. In some embodiments, the clamping arm can be releasably locked in a position with respect to the receiving arm. In some embodiments, a locking mechanism can be released (can be moved to an unlocked configuration) before the clamping arm is moved towards the receiving arm.

A sliding component coupled to the clamping arm is moved in a first direction along a track of the clamping arm toward the receiving arm such that a needle of the sliding component is moved into the body of the patient and is coupled to the portion of the implant (block 830). The sliding component can be moved after a locking mechanism has been released (is moved to an unlocked configuration). In some embodiments, the sliding component can be biased away from the receiving arm so that a force must be applied to the sliding component to move the sliding component towards the receiving arm. The needle can have a coupling component configured to be coupled to the portion of the implant. In some embodiments, the sliding component can be biased toward the receiving arm so that the sliding component moves toward the receiving arm in response to a locking mechanism being released.

The sliding component coupled to the clamping arm moved in a second direction along the track of the clamping arm away from the receiving arm until the portion of the implant coupled to the needle of the sliding component is moved outside of the body of the patient (block 840). In some embodiments, the clamping arm can be biased (e.g., biased with a spring mechanism) away from the receiving arm so that the clamping arm automatically moves away from the receiving arm and pulls the portion of the implant (and the needle) out of the body of the patient.

Figure 9:
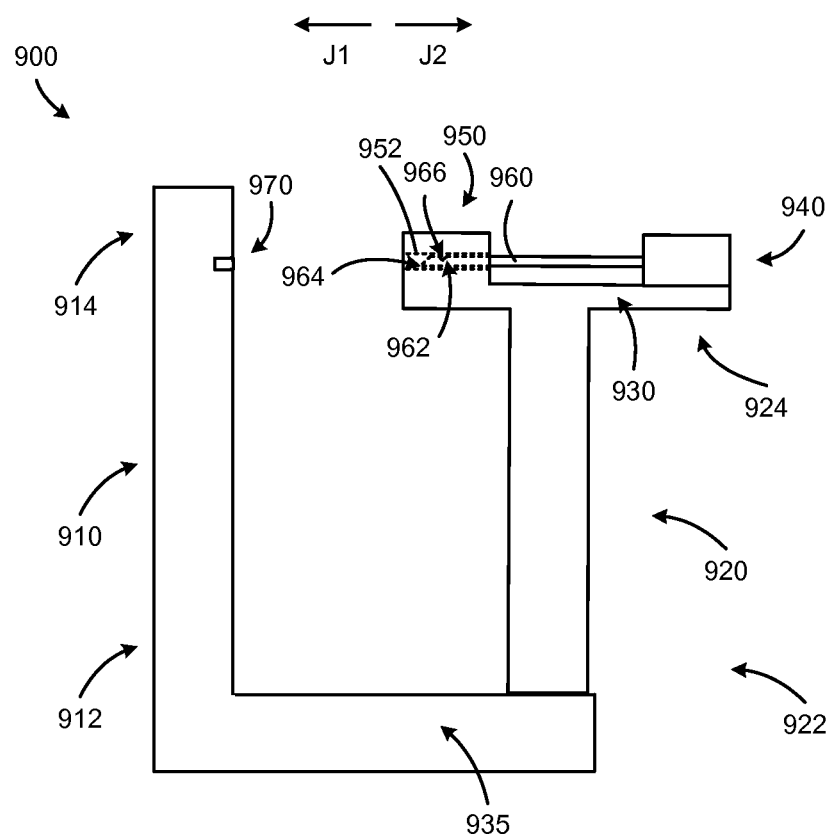
FIG. 9 illustrates yet another medical device, according to an embodiment.

FIG. 9 illustrates yet another medical device 900, according to an embodiment. The medical device 900 is configured to be used as an insertion tool or delivery tool to implant or insert a bodily implant (not shown) into a body of a patient (e.g., using an outside-in approach via a vaginal incision in the body of the patient).

As shown in FIG. 9, the medical device 900 has a receiving arm 910 coupled to a clamping arm 920. The clamping arm 920 can be moved (e.g., slidably moved) with respect to the receiving arm 910 in a direction J1 and/or a direction J2 along a track 935 of the receiving arm 910. The track 935 can be similar to the tracks described above. The medical device 900 shown in FIG. 9 is in an open configuration, in some embodiments, the medical device 900 can also be moved to a clamped configuration.

Although the track 935 is shown as being included in (or associated with) the receiving arm 910, in some embodiments, the track 935 can be included in (or associated with) the clamping arm 920. In some embodiments, the track 935 can be a separate component (e.g., a track component) along which both the receiving arm 910 and the clamping arm 920 can be slidably moved. In such embodiments, the receiving arm 910 and the clamping arm 920 can be independently slidably moved along the track 935.

Also, as shown in FIG. 9, a sliding component 940 may be slidably moved along a track 930 (e.g., a track associated with the sliding component 940) in the direction J1 (towards a coupling mechanism 970) and/or the direction J2 (away from the coupling mechanism 970). The sliding component 940 is shown in a stowed configuration in FIG. 9 (where a distal portion 962 of the needle 960 is disposed within a lumen 952 of a guide 950). In some embodiments, the sliding component 940 may also be moved to a deployed configuration. The sliding component 940 is coupled to (or includes) a needle 960 that is configured to slidably move within the lumen 952 of the guide 950. Although shown as a straight track 930 and a straight needle 960 in FIG. 9, in some embodiments, the track 930 and the needle 960 can be curved.

Medical device 900 shown in FIG. 9 can include any of the features described in connection with and/or shown in the medical devices above. For example, medical device 900 can include one or more locking mechanisms, indicator mechanisms, ratchet mechanisms, syringes, and/or so forth.

In some embodiments, the sliding component 940 can be slidably moved along the track 930 using a device configured to apply a force to the sliding component 940. For example, sliding component 940 can be moved along direction J1 and/or direction J2 using a motor. In some embodiments, the motor can be installed inside of the sliding component 940 and can be actuated by physician using a button coupled to the medical device. In some embodiments, the sliding component 940 can be slidably moved along the track 930 using, for example, a ball-screw mechanism (not shown) coupled to a motor. Similarly, the clamping arm 920 and the receiving arm 910 can be moved toward one another using a device configured to apply a force to the clamping arm 920 and/or the receiving arm 910. One or more of the medical devices described above can incorporate a device (e.g., a motor) configured to slidably move a sliding mechanism and/or rotatably move portions of the medical devices.

Figure 10:
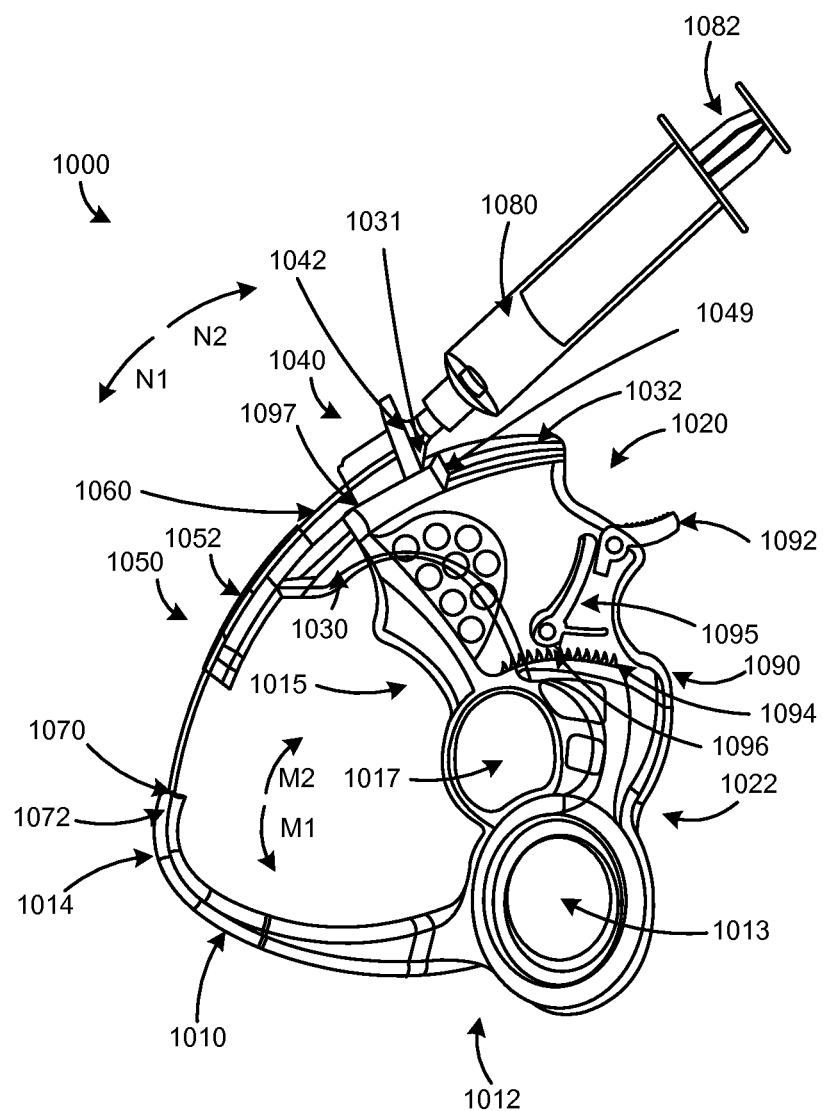
FIG. 10 illustrates yet another medical device, according to an embodiment.

FIG. 10 illustrates yet another medical device 1000 according to an embodiment. Some portions of FIG. 10 are shown in "see-through" so that at least some internal components may be viewed. In some embodiments, some portions of the medical device 1000, when implemented, may be translucent and some portions of the medical device 1000, when implemented, may not be translucent. The medical device 1000 is configured to be used as an insertion tool or delivery tool to implant or insert a bodily implant (not shown) into a body of a patient. As shown in FIG. 10, the medical device 1000 has a receiving arm 1010 coupled (e.g., hingedly coupled) to a clamping arm 1020. The clamping arm 1020 can be moved (e.g., rotatably moved) with respect to the receiving arm 1010 in a direction M1 and/or a direction M2. The medical device 1000 shown in FIG. 10 is in a clamped configuration, in some embodiments, the medical device 1000 can also be moved to an open configuration. In this embodiment, the receiving arm 1010 of the medical device 1000 has a proximal portion 1012 hingedly coupled to a proximal portion 1022 of the clamping arm 1020 of the medical device 1000.

As shown in FIG. 10, a sliding component 1040 may be slidably moved along a track 1030 in direction N1 (towards a coupling mechanism 1070) and/or direction N2 (away from the coupling mechanism 1070). In this embodiment, the coupling mechanism 1070 defines a cavity 1072. As shown in FIG. 10, the track 1030 has a groove 1032 along which sliding component 1040 slidably moves.

The sliding component 1040 is shown in a deployed configuration in FIG. 10 (where a distal portion 1062 of a needle 1060 is disposed outside of a lumen 1052 of a guide 1050). In some embodiments, the sliding component 1040 may also be moved to a stowed configuration (not shown). The needle 1060 is coupled to the sliding component 1040 and is configured to slidably move within the lumen 1052 of the guide 1050. Although not shown in FIG. 10, the sliding component 1040 can include a locking mechanism configured to releasably lock the sliding component 1040 in a position along the track 1030.

As shown in FIG. 10, the receiving arm 1010 has a trigger handle 1015 such that the receiving arm 1010 defines approximately a V-shape. In this embodiment, at least a portion of the trigger handle 1015 of the receiving arm 1010 is disposed within the clamping arm 1020. The trigger handle 1015 also includes an opening 1017 into which a finger of a physician may be inserted. In some embodiments, the trigger handle 1015 may not have a portion disposed within the clamping arm 1020. The clamping arm 1020 can be moved towards, or over, at least a portion of the trigger handle 1015 of the receiving arm 1010 such that the track 1030 and guide 1050 of the clamping arm 1020 are moved towards the coupling mechanism 1070. For example, a physician can grasp the trigger handle 1015 with one or more fingers so that a heel or palm of the physician's hand (or another portion of the physician's hand) is against the clamping arm 1020. The physician can squeeze the medical device 1000 so that the clamping arm 1020 is moved towards, or over, at least a portion of the trigger handle 1015 of the receiving arm 1010. In some embodiments, the medical device 1000 may be squeezed more than once during a medical procedure until the clamping arm 1020 is moved to a desirable position with respect to the receiving arm 1010, or a portion thereof (e.g., the coupling mechanism 1070 of the receiving arm 1010). In some embodiments, the clamping arm 1020 may be moved along direction Ml more than once and/or along direction M2 more than once so that the clamping arm 1020 may be moved to a desirable position with respect to the receiving arm 1010, or a portion thereof, during a medical procedure.

As shown in FIG. 10, the medical device 1000 has a locking mechanism 1090 configured to lockably couple the clamping arm 1020 with respect to the receiving arm 1010. In this embodiment, the locking mechanism 1090 can be referred to as a ratchet mechanism. The locking mechanism 1090 can be used to releasably lock the medical device 1000 in one or more open configurations and/or one or more clamped configurations. In this embodiment, the locking mechanism 1090 can be configured to releasably lock the clamping arm 1020 with respect to the receiving arm 1010 as the clamping arm 1020 is moved towards, or over, at least a portion of the trigger handle 1015 of the receiving arm 1010. For example, the locking mechanism 1090 can be configured to releasably lock the clamping arm 1020 with respect to the receiving arm 1010 as a physician squeezes the medical device 1000 so that the clamping arm 120 is moved towards, or over, at least a portion of the trigger handle 1015 of the receiving arm 1010.

In some embodiments, a physician may squeeze the medical device 1000 during a first time period (starting at a first time) so that the clamping arm 1020 is lockably coupled using the locking mechanism 1090 in a first position with respect to the receiving arm 1010 (e.g., the coupling mechanism 1070 of the receiving arm 1010). In some embodiments, the physician may squeeze the medical device 1000 during a second time period (after the first time period and starting at a second time) so that the clamping arm 1020 is lockably coupled using the locking mechanism 1090 in a second position with respect to the receiving arm 1010 (e.g., the coupling mechanism 1070 of the receiving arm 1010). In some embodiments, the clamping arm 1020 may be closer to the receiving arm 1010 when the clamping arm 1020 is in the first position with respect to the receiving arm 1010 (or a portion thereof) than when the clamping arm 1020 is in the second position with respect to the receiving arm 1010 (or a portion thereof). In some embodiments, the locking mechanism 1090 may be released (e.g., released by the physician) one or more times by the physician between the first time period and the second time period. In such embodiments, the clamping arm 1020 may be moved away from the receiving arm 1010 (or a portion thereof) along direction M2 after the locking mechanism 1090 has been released. In such embodiments, the clamping arm 1020 may be farther from the receiving arm 1010 when the clamping arm 1020 is in the first position with respect to the receiving arm 1010 (or a portion thereof) than when the clamping arm 1020 is in the second position with respect to the receiving arm 1010 (or a portion thereof).

In the illustrated embodiment, the locking mechanism 1090 has protrusions 1094 (e.g., teeth) that can be configured to be coupled to (e.g., contact, catch on) a protrusion 1096 disposed within the clamping arm 1020 (and facing the protrusions 1094) and included in rotatable mechanism 1095. The protrusions 1094, when coupled to (e.g., contacted with) the protrusion 1096, can lock a position of the receiving arm 1010 with respect to a position of the clamping arm 1020. The coupling of one or more of the protrusions 1094 to the protrusion 1096 can be released using a rotatable lever 1092, which is configured to contact and push against a lever of rotatable mechanism 1095. In some embodiments, the locking mechanism 1090 can be biased (via the rotatable lever 1092) towards a locked configuration (e.g., being lockably coupled), or biased to an unlocked configuration.

In this embodiment, the proximal portion 1022 of the clamping arm 1020 and the proximal portion 1012 of the receiving arm 1010 collectively define a finger hole 1013. Also, in this embodiment, the proximal portion 1022 of the clamping arm 1020 and the proximal portion 1012 of the receiving arm 1010 are hingedly coupled at the finger hole 1013. The finger hole 1013 can be used by, for example, a physician to grasp the medical device 1000. In some embodiments, the finger hole 1013 can be defined by only the proximal portion 1022 of the clamping arm 1020 or the proximal portion 1012 of the receiving arm 1010. In some embodiments, the proximal portion 1022 of the clamping arm 1020 and the proximal portion 1012 of the receiving arm 1010 are not hingedly coupled at the finger hole 1013.

As shown in FIG. 10, the medical device 1000 includes an indicator member 1097, which is part of (e.g., integrated as part of) the trigger handle 1015. The indicator member 1097 is configured to align with one or more of the indicators 1031 (e.g., numbers, marks, detents) associated with (aligned along) the track 1030. In some embodiments, the indicator member 1097 and the indicators 1031 can collectively define an indicator mechanism. In some embodiments, the indicator member 1097, when aligned with one or more of the indicators 1031, can indicate, for example, a distance between at least a portion of the receiving arm 1010 (e.g., the coupling mechanism 1070) and at least a portion of the clamping arm 1020 (e.g., the track 1030, a distal portion of the guide 1050). In other words, one or more of the indicators 1031 (when pointed to by the indicator member 1097) can be an indicator of a relative positions (when the medical device 1000 is in an open configuration and/or a clamped configuration) of at least a portion of the receiving arm 1010 and at least a portion of the clamping arm 1020. In some embodiments, at least a portion of the track 1030 may be translucent (for example, formed of a translucent material) so that the indicator member 1097 may be visible to a physician using the medical device 1000.

In some embodiments, the indicator member 1097 can also be configured to limit movement of the sliding component 1040. For example, as shown in FIG. 10, the indicator member 1097 can be configured to prevent the sliding component 1040 from movement to a position beyond the indicator member 1097. The sliding component 1040 can have a protrusion (e.g., a tab) (not shown) that limits (e.g., stops) the movement of the sliding component 1040 when the protrusion comes into contact with the indicator member 1097.

In some embodiments, the indicator member 1097, when aligned with one or more of the indicators 1031, can indicate, for example, a target position of the sliding component 1040 along the track 1030. The target position can be a position at which at least a portion of the needle 1060 is, for example, moved into or near the cavity 1072 of the coupling mechanism 1070 so that the needle 1060 is coupled to at least a portion of an implant coupled to the coupling mechanism 1070. In some embodiments, the target position can be a position at which at least a portion of the needle 1060 comes into contact with at least a portion of an implant coupled to the coupling mechanism 1070.

In some embodiments, the indicator member 1097 can be configured so that a distal portion of the needle 1060 will precisely move into the cavity 1072 of the coupling mechanism 1070 of the receiving arm 1010. For example, the receiving arm 1010 can be moved towards the clamping arm 1020 so that a distal end (a front portion) of the guide 1050 is a distance from the coupling mechanism 1070. The indicator member 1097 can be configured to limit the movement of the sliding component so that the portion of the needle 1060 that is extended from (deployed from) the distal end of the guide 1050 has a length that is approximately equal to, slightly greater than, or equal to the distance.

As shown in FIG. 10, the sliding component 1040 includes a locking mechanism 1049 configured to releasably lock the sliding component 1040 in a position along the track 1030. In some embodiments, the sliding component 1040 can be releasably locked in any position along the track 1030 using the locking mechanism 1049 (e.g., a protrusion, a tab). For example, the sliding component 1040 can be releasably locked in the deployed configuration shown in FIG. 10.

In some embodiments, the locking mechanism 1049 can be biased so that the sliding component 1040 may not be moved along the track 1030 unless the locking mechanism 1049 is actuated. In other words, the locking mechanism 1049 can be configured so that the locking mechanism 1049 can be actuated to release the locking mechanism so that the sliding component 1040 may be slidably moved along the track 1030. In some embodiments, the locking mechanism 1049 can be biased so that the sliding component 1040 may not be locked into a position along the track 1030 until actuated using the locking mechanism 1049. In other words, the locking mechanism 1049 can be configured so that the locking mechanism 1049 can be actuated to lock the sliding component 1040 along the track 1030.

In the embodiment shown in FIG. 10 the needle 1060 of the medical device 1000 is configured to convey a fluid. The needle 1060 can define a lumen that is configured to convey fluids to and/or from a body of a patient. As shown in FIG. 10, the sliding component 1040 is coupled at 1042 to a syringe 1080 that has a plunger 1082. The syringe 1080 is configured to deliver a fluid to and/or draw a fluid from the needle 1060.

Figure 11A:
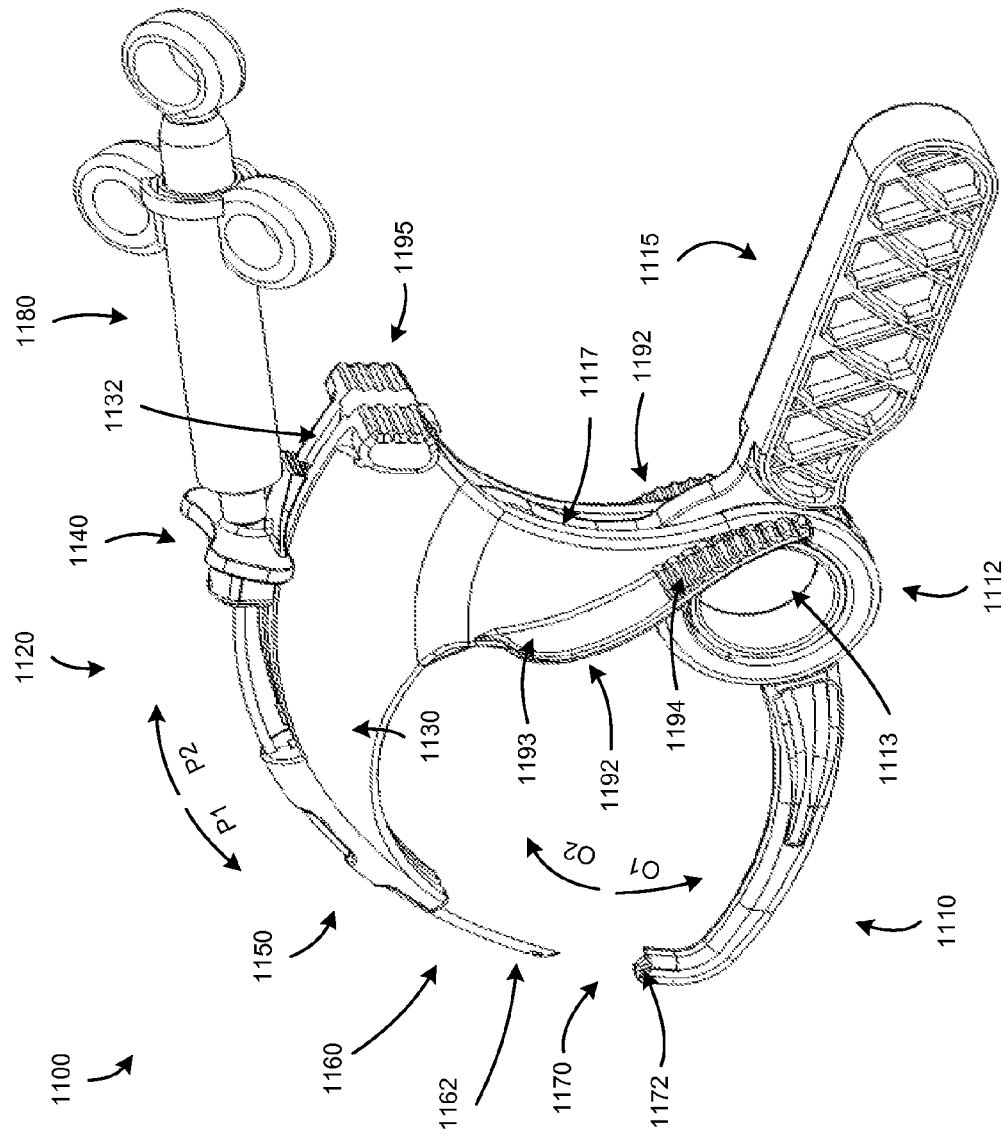
Figure 11B:
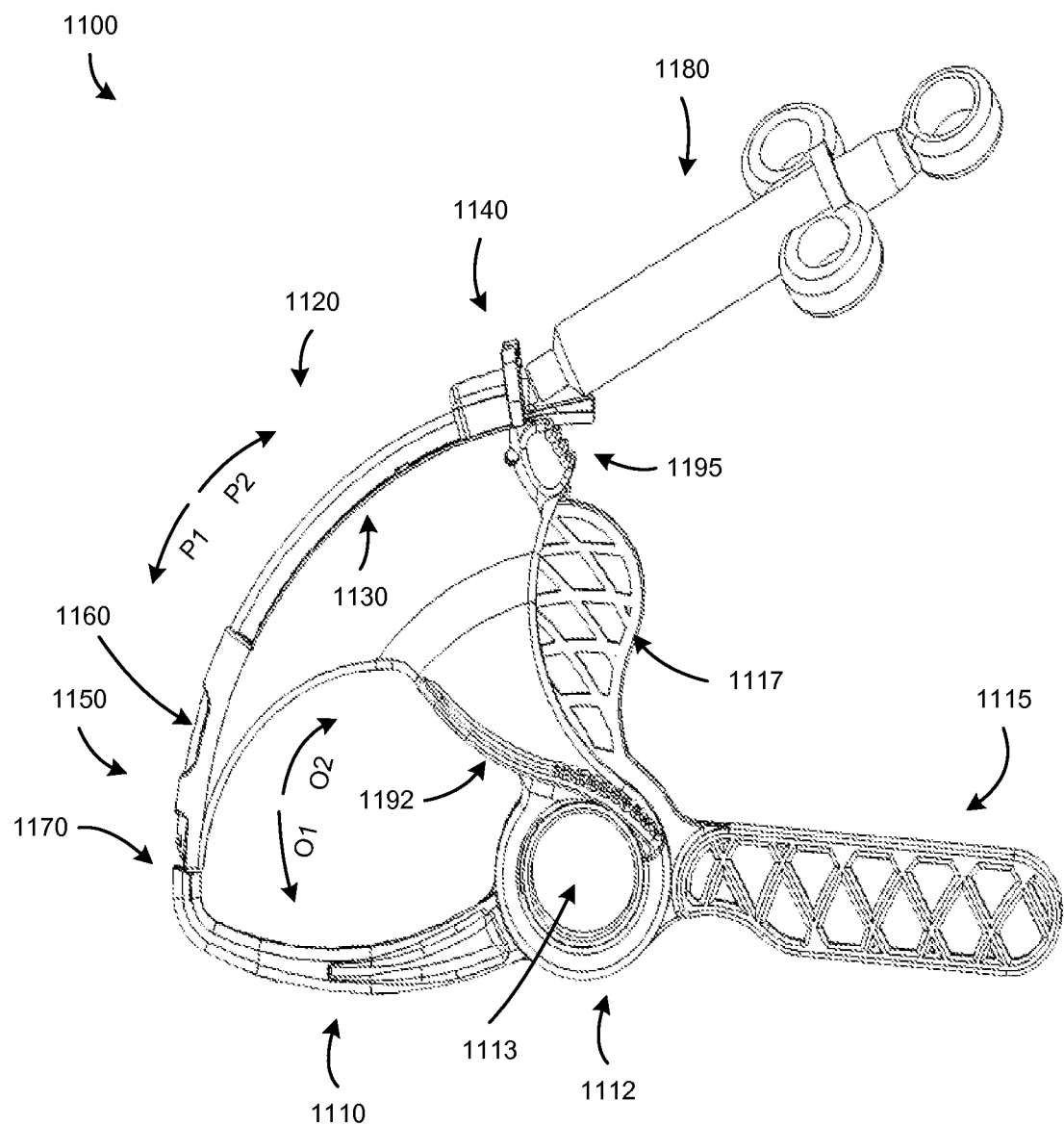
Figure 11C:
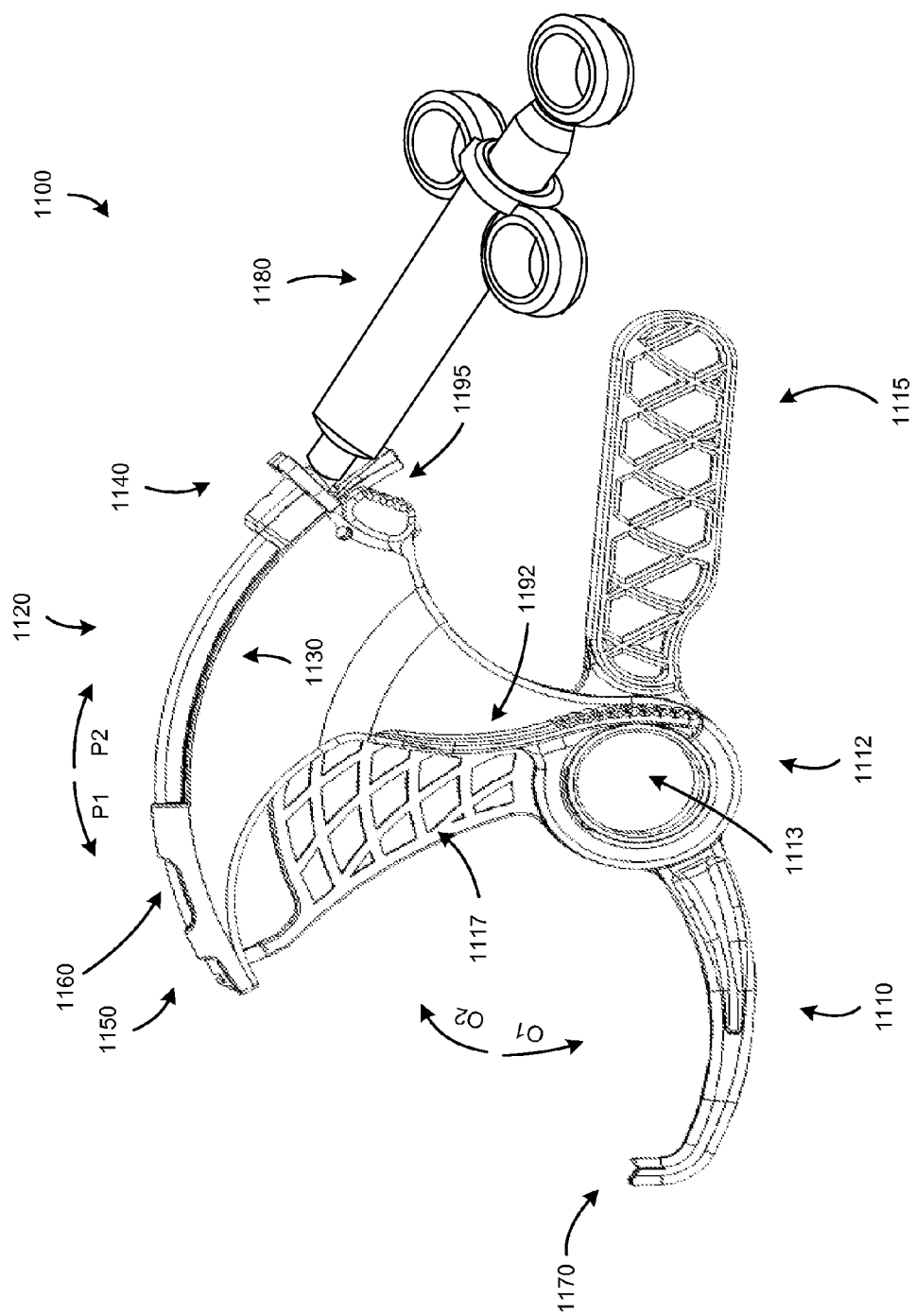
Figure 11D:
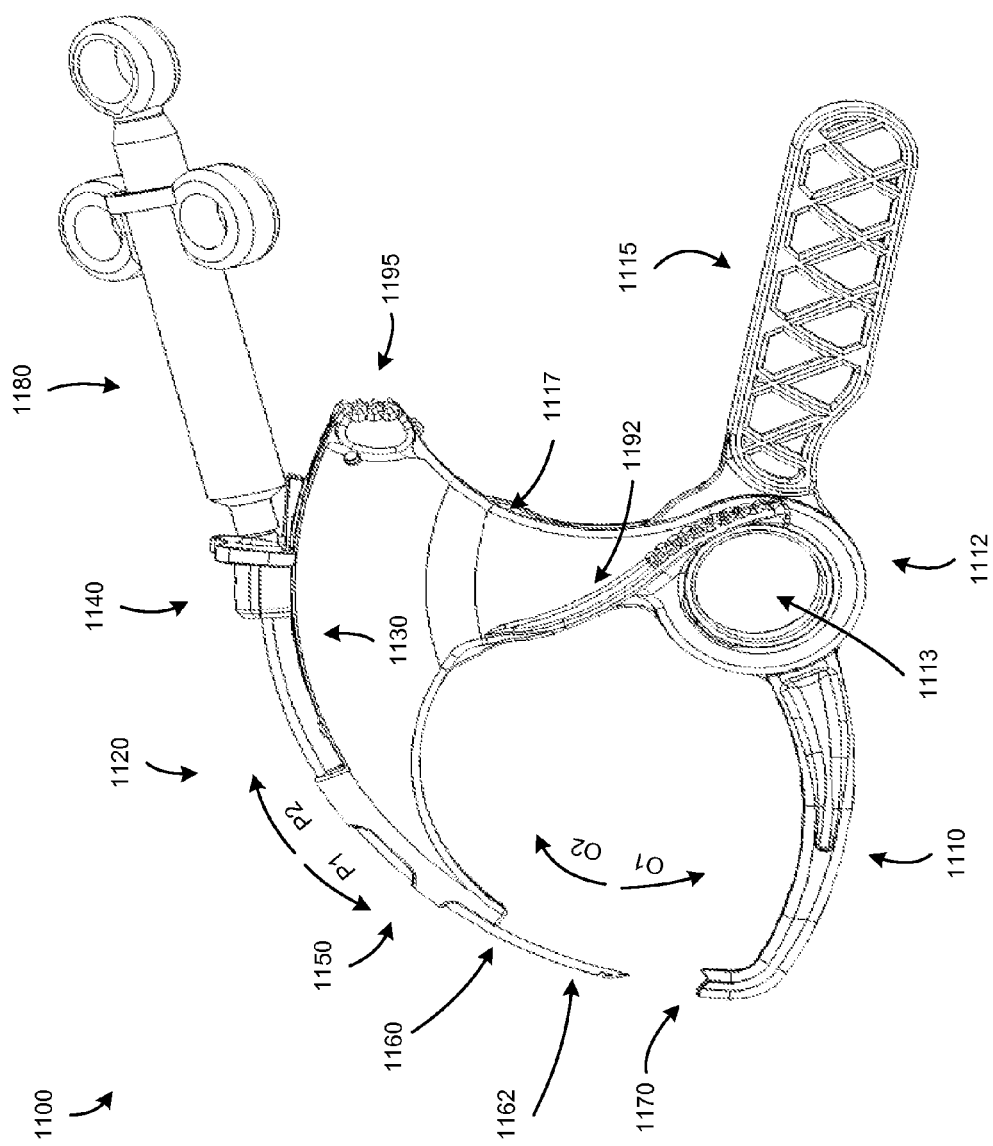

FIGS. 11A through 11I illustrate yet another medical device 1100 according to an embodiment. Some portions of the figures (e.g., FIGS. 11C and 11E) are shown in "see-through" so that at least some internal components may be viewed. In some embodiments, some portions of the medical device 1100, when implemented, may be translucent and some portions of the medical device 1100, when implemented, may not be translucent. The medical device 1100 is configured to be used as an insertion tool or delivery tool to implant or insert a bodily implant (not shown) into a body of a patient. As shown in FIG. 11A, the medical device 1100 has a receiving arm 1110 coupled (e.g., hingedly coupled) to a clamping arm 1120. The clamping arm 1120 can be moved (e.g., rotatably moved) with respect to the receiving arm 1110 in a direction 01 and/or a direction 02. The medical device 1100 shown in FIG. 11A (and also shown in, for example, FIG. 11B) is in a clamped configuration, in some embodiments, the medical device 1100 can also be moved to an open configuration as shown in FIG. 11C and FIG. 11G.

In this embodiment, the receiving arm 1110 of the medical device 1100 has a portion hingedly coupled at a hinge 1112 to a portion of the clamping arm 1120 of the medical device 1100. In this embodiment, the portion of the receiving arm 1110 of the medical device 1100 and the portion of the clamping arm 1120 of the medical device 1100 collectively define a finger hole 1113. Thus, in this embodiment, the portion of the clamping arm 1120 and the portion of the receiving arm 1110 are hingedly coupled at the finger hole 1113. The finger hole 1113 can be used by, for example, a physician to grasp the medical device 1100. Although not shown, in some embodiments, the finger hole 1113 can be defined by only a portion of the clamping arm 1120 or only a portion of the receiving arm 1110. In some embodiments, the proximal portion 1122 of the clamping arm 1120 and the proximal portion 1112 of the receiving arm 1110 are not hingedly coupled at the finger hole 1113.

As shown in FIG. 11A, a sliding component 1140 may be slidably moved along a track 1130 in direction P1 (towards a coupling mechanism 1170) and/or direction P2 (away from the coupling mechanism 1170). In this embodiment, the coupling mechanism 1170 defines a cavity 1172. As shown in FIG. 11A, the track 1130 has a groove 1132 along which sliding component 1140 slidably moves.

The sliding component 1140 is shown in a deployed configuration in FIG. 11A (also shown at least in FIGS. 11D, 11E, 11H, and 11I) where a distal portion 1162 of a needle 1160 is disposed outside of a lumen of a guide 1150. In this embodiment, the guide 1150 includes multiple sections and defines multiple lumens. In some embodiments, the sliding component 1140 may also be moved to a stowed configuration (shown at least in FIGS. 11B, 11C, 11F, and 11G). The needle 1160 is coupled to the sliding component 1140 and is configured to slidably move within the lumen of the guide 1150.

As shown in at least FIG. 11A, the medical device 1100 includes side protrusions 1192 (also can be referred to as tabs) coupled to at least a portion of the clamping arm 1120. One or more of the side protrusions 1192 can be used by a physician to push (e.g., push using a thumb) the clamping arm 1120 toward the receiving arm 1110 (from an open configuration (such as that shown in FIG. 11C and FIG. 11G) to a clamped configuration (such as that shown in FIG. 11A)). In some embodiments, one or more of the side protrusions 1192 can be used to hold the medical device 1100 in a clamped configuration after the medical device 1100 has been moved to the clamped configuration using one or more of the side protrusions 1192. In some embodiments, one or more of the side protrusions 1192 can be used (e.g., using a pulling motion) to move the medical device 1100 from a clamped (or closed configuration) to an open configuration.

As shown in at least FIG. 11A, the side protrusions 1192 have a smooth portion 1193 (e.g., relatively smooth portion) and a rough portion 1194 (e.g., a relatively rough portion). The smooth portion 1193 can be configured so that a portion (e.g., a thumb) of a hand of a physician may slide (e.g., slidably move) along the smooth portion 1193 as the smooth portion 1193 of the side protrusion 1192 is used to move the clamping arm 1120 toward the receiving arm 1110. The rough portion 1194 can be configured so that a portion (e.g., a thumb) of a hand of a physician may be prevented from sliding (e.g., slidably moving) along the rough portion 1194 as the smooth portion 1194 of the side protrusion 1192 is used to move the clamping arm 1120 toward the receiving arm 1110.

In this embodiment, the rough portion 1192 is defined by a bumpy surface. In some embodiments, the smooth portion 1193 and/or the rough portion 1194 may be defined by various elements that are different than those shown in at least FIG. 11A. For example, the rough portion 1194 can include, or can be made of, a rough adhesive substance such as sandpaper, a sticky substance, circular bumps, and/or so forth. Although not shown in FIG. 11A, in some embodiments, a single side protrusion 1192 may have multiple smooth portions and/or multiple rough portions.

As shown in at least FIG. 11A, the medical device 1100 includes top protrusions 1195 (also can be referred to as tabs) coupled to at least a portion of the clamping arm 1120. One or more of the top protrusions 1195 can be used by a physician to push (e.g., push using a thumb) the clamping arm 1120 toward the receiving arm 1110 (from an open configuration (such as that shown in FIG. 11C and FIG. 11G) to a clamped configuration (such as that shown in FIG. 11A)). In some embodiments, one or more of the top protrusions 1195 can be used to hold the medical device 1100 in a clamped configuration after the medical device 1100 has been moved to the clamped configuration using one or more of the top protrusions 1195. In some embodiments, one or more of the top protrusions 1195 can be used (e.g., using a pulling motion) to move the medical device 1100 from a clamped (or closed configuration) to an open configuration.

In this embodiment, the top protrusions 1195 each have a rough portion that is defined by a bumpy surface. In some embodiments, the surfaces of the rough portions of the top protrusions 1195 may be defined by various elements that are different than those shown in at least FIG. 11A. For example, the top protrusions 1195 can have a surface that includes, or can be made of, a rough adhesive substance such as sandpaper, a sticky substance, circular bumps, and/or so forth. Although not shown in FIG. 11A, in some embodiments, one or more of the top protrusions 1195 may not have a have a rough portion.

In some embodiments, one or more of the side protrusions 1192 and/or one or more of the top protrusions 1195 can be used by a physician to maneuver the medical device 1100 when, for example, moving the receiving arm 1110 into a body of a patient. In some embodiments, the medical device 1100 can have a single side protrusion rather than two side protrusions 1192 as shown in FIG. 11A, and/or can have a single top protrusion rather than two top protrusions 1195 as shown in FIG. 11A. In some embodiments, the medical device 1100 can have a more than two side protrusions, and/or can have a more than two top protrusions. In some embodiments, the shape of the side protrusions 1192 and/or the top protrusions 1195 can be different than those shown in FIG. 11A. In some embodiments, the side protrusions 1192 and/or the top protrusions 1195 can have a triangular profile, can have a square profile, may not have a curved profile, and/or so forth.

In some embodiments, the medical device 1100 may be biased (e.g., bias using a spring mechanism) to an open configuration. Accordingly, one or more of the side protrusions 1192 and/or one or more of the top protrusions 1195 can be used to move the medical device 1100 from the open configuration to a closed configuration by applying a force (e.g., by a physician) to the side protrusion(s) 1192 and/or the top protrusion(s) 1195. When the force is no longer applied to the side protrusion(s) 1192 and/or the top protrusion(s) 1195, the medical device 1100 may move back to the open configuration in response to the biasing.

In some embodiments, a physician may move, using one or more of the side protrusions 1192 and/or one or more of the top protrusions 1195, the medical device 1100 during a first time period (starting at a first time) so that the clamping arm 1120 is moved to a first position with respect to the receiving arm 1110 (e.g., the coupling mechanism 1170 of the receiving arm 1110). In some embodiments, the physician may move, using one or more of the side protrusions 1192 and/or one or more of the top protrusions 1195, the medical device 1100 during a second time period (after the first time period and starting at a second time) so that the clamping arm 1120 is moved to a second position with respect to the receiving arm 1110 (e.g., the coupling mechanism 1170 of the receiving arm 1110). In some embodiments, the clamping arm 1120 may be closer to the receiving arm 1110 when the clamping arm 1120 is in the first position with respect to the receiving arm 1110 (or a portion thereof) than when the clamping arm 1120 is in the second position with respect to the receiving arm 1110 (or a portion thereof). In some embodiments, a force applied by the physician against one or more of the side protrusions 1192 may be released (e.g., released by the physician) one or more times by the physician between the first time period and the second time period. In such embodiments, the clamping arm 1120 may be moved away from the receiving arm 1110 (or a portion thereof) along direction 02 after being released. In such embodiments, the clamping arm 1120 may be farther from the receiving arm 1110 when the clamping arm 1120 is in the first position with respect to the receiving arm 1110 (or a portion thereof) than when the clamping arm 1120 is in the second position with respect to the receiving arm 1110 (or a portion thereof).

As shown in at least FIG. 11A, the medical device 1100 includes a handle 1115. In some embodiments, the handle 1115 can be used by a physician to maneuver the medical device 1100 when, for example, moving the receiving arm 1110 into a body of a patient. In this embodiment, at least a portion of the handle 1115 is coupled to a portion 1117 disposed within the clamping arm 1120 when the medical device 1100 is in the configuration shown in FIG. 11A.

The clamping arm 1120 can be moved over at least the portion 1117 of the receiving arm 1110 as the track 1130 and guide 1150 of the clamping arm 1120 are moved towards or away from the coupling mechanism 1170. For example, a physician can grasp the portion 1117 with one or more fingers so that a heel or palm of the physician's hand (or another portion of the physician's hand) is against the clamping arm 1120. The physician can squeeze the medical device 1100 while the medical device 1100 is in the configuration shown in FIG. 11C (or FIG. 11G) so that the clamping arm 1120 is moved towards, or over, at least the portion 1117 of the receiving arm 1110 toward the configuration shown in FIG. 11A (or FIG. 11H or FIG. 11I) or the configuration shown in FIG. 11B (or FIG. 11F). While in the configuration shown in FIG. 11A, the portion 1117 is substantially disposed within the clamping arm 1120. At least a first portion of the portion 1117 is substantially disposed on one side of the clamping arm 1120 while in the configuration shown in FIG. 11B, and at least a second portion of the portion 1117 is substantially disposed on another side of the clamping arm 1120 while in the configuration shown in FIG. 11C. In some embodiments, the medical device 1100 may be squeezed more than once during a medical procedure until the clamping arm 1120 is moved to a desirable position with respect to the receiving arm 1110, or a portion thereof (e.g., the coupling mechanism 1170 of the receiving arm 1110). In some embodiments, the clamping arm 1120 may be moved along direction 01 more than once and/or along direction O2 more than once so that the clamping arm 1120 may be moved to a desirable position with respect to the receiving arm 1110, or a portion thereof, during a medical procedure. In some embodiments, the handle 1115 may not be coupled to the portion 1117 that has a portion disposed within the clamping arm 1120.

Figure 11E:
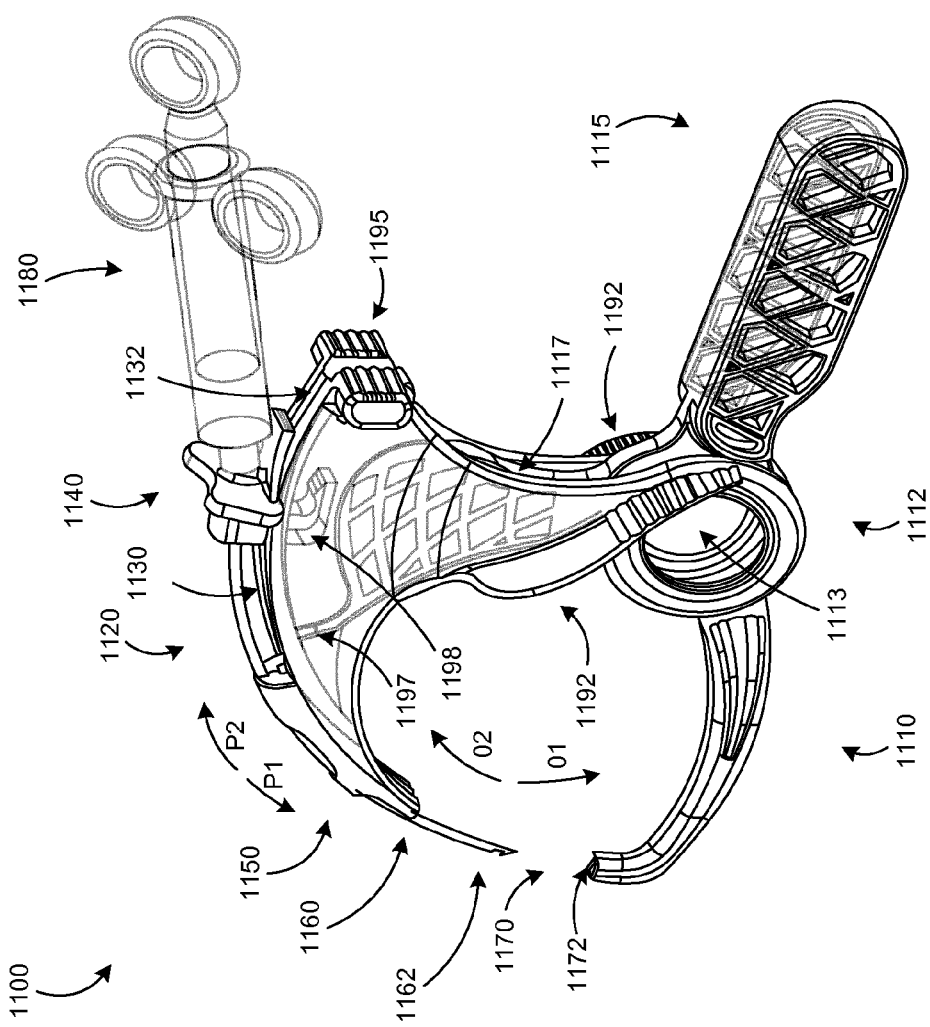
Figure 11I:
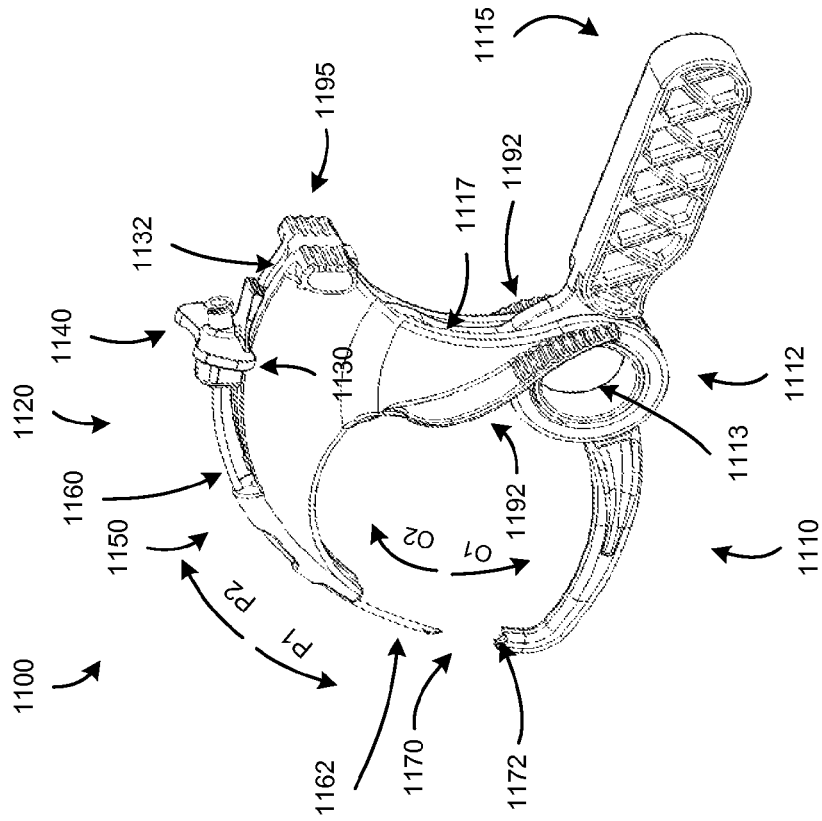
Figure 11H:
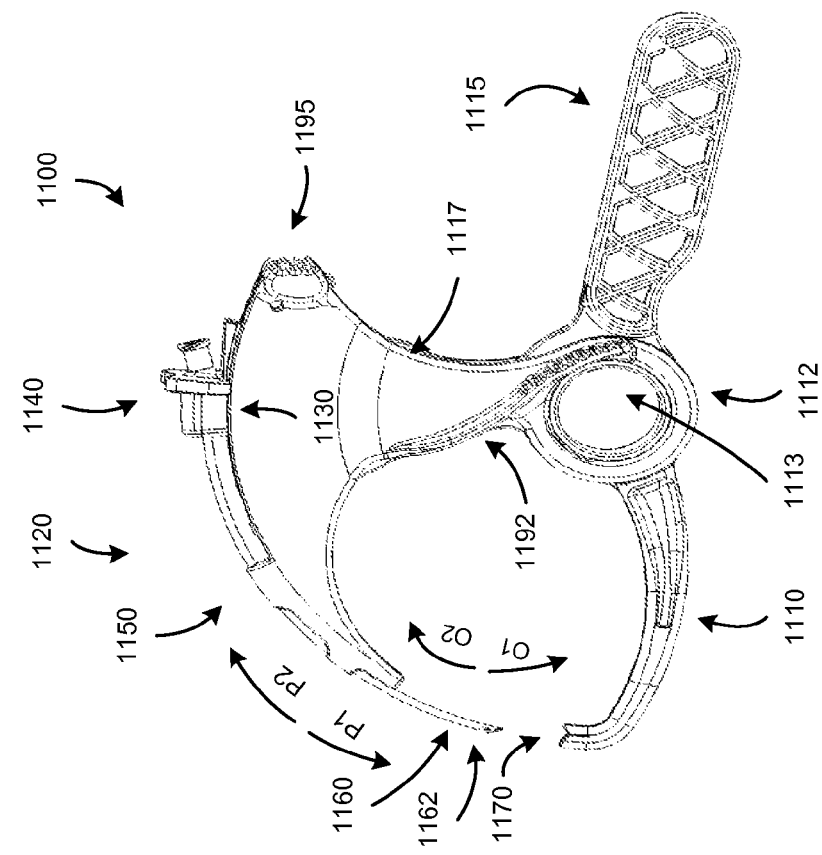

As shown in FIG. 11E, the medical device 1100 includes an indicator member 1197, which is part of (e.g., integrated as part of) the portion 1117. The indicator member 1197 can be configured to align with one or more of indicators (not shown) (e.g., numbers, marks, detents) associated with (aligned along) the track 1130. In some embodiments, the indicator member 1197 and the indicators can collectively define an indicator mechanism. In some embodiments, the indicator member 1197 can indicate, for example, a distance between at least a portion of the receiving arm 1110 (e.g., the coupling mechanism 1170) and at least a portion of the clamping arm 1120 (e.g., the track 1130, a distal portion of the guide 1150). In some embodiments, at least a portion of the track 1130 may be translucent (for example, formed of a translucent material) so that the indicator member 1197 may be visible to a physician using the medical device 1100.

In some embodiments, the indicator member 1197 can also be configured to limit movement of the sliding component 1140. For example, as shown in FIG. 11, the indicator member 1197 can be configured to prevent the sliding component 1140 from movement to a position beyond the indicator member 1197. The sliding component 1140 has a protrusion 1198 (e.g., a tab) that limits (e.g., stops) the movement of the sliding component 1140 when the protrusion 1198 comes into contact with the indicator member 1197.

In some embodiments, the indicator member 1197, when aligned with one or more indicators along the track 1130, can indicate, for example, a target position of the sliding component 1140 along the track 1130. The target position can be a position at which at least a portion of the needle 1160 is, for example, moved into or near the cavity 1172 of the coupling mechanism 1170 so that the needle 1160 is coupled to at least a portion of an implant coupled to the coupling mechanism 1170. In some embodiments, the target position can be a position at which at least a portion of the needle 1160 comes into contact with at least a portion of an implant coupled to the coupling mechanism 1170.

In some embodiments, the indicator member 1197 can be configured so that a distal portion of the needle 1160 will precisely move into the cavity 1172 of the coupling mechanism 1170 of the receiving arm 1110. For example, the receiving arm 1110 can be moved towards the clamping arm 1120 so that a distal end (a front portion) of the guide 1150 is a distance from the coupling mechanism 1170. The indicator member 1197 can be configured to limit the movement of the sliding component so that the portion of the needle 1160 that is extended from (deployed from) the distal end of the guide 1150 has a length that is approximately equal to, slightly greater than, or equal to the distance.

Although not shown in FIGS. 11A through 11E, the sliding component 1140 can include a locking mechanism configured to releasably lock the sliding component 1140 in a position along the track 1130. In some embodiments, the sliding component 1140 can be releasably locked in any position along the track 1130 using the locking mechanism (e.g., a protrusion, a tab). In some embodiments, the locking mechanism can be biased so that the sliding component 1140 may not be moved along the track 1130 unless the locking mechanism is actuated. In other words, the locking mechanism can be configured so that the locking mechanism can be actuated to release the locking mechanism so that the sliding component 1140 may be slidably moved along the track 1130. In some embodiments, the locking mechanism can be biased so that the sliding component 1140 may not be locked into a position along the track 1130 until actuated using the locking mechanism. In other words, the locking mechanism can be configured so that the locking mechanism can be actuated to lock the sliding component 1140 along the track 1130.

Although not shown in FIGS. 11A through 11E, the medical device 1100 can have a locking mechanism configured to lockably couple the clamping arm 1120 with respect to the receiving arm 1110. In this embodiment, the locking mechanism can be referred to as a ratchet mechanism. The locking mechanism can be used to releasably lock the medical device 1100 in one or more open configurations and/or one or more clamped configurations. In this embodiment, the locking mechanism can be configured to releasably lock the clamping arm 1120 with respect to the receiving arm 1110 as the clamping arm 1120 is moved towards, or over, at least a portion of the portion 1117 of the receiving arm 1110. For example, the locking mechanism can be configured to releasably lock the clamping arm 1120 with respect to the receiving arm 1110 as a physician squeezes the medical device 1100 so that the clamping arm 120 is moved towards, or over, at least a portion of the portion 1117 of the receiving arm 1110.

In the embodiment shown in at least FIG. 11A the needle 1160 of the medical device 1100 is configured to convey a fluid. The needle 1160 can define a lumen that is configured to convey fluids to and/or from a body of a patient. As shown in FIG. 11A, the sliding component 1140 is coupled to a syringe 1180 that has a plunger (also shown in FIGS. 11B through 11E). The syringe 1180 is configured to deliver a fluid to and/or draw a fluid from the needle 1160.

In one general aspect, a medical device can include a receiving arm configured to be coupled to at least a portion of an implant, a clamping arm having a proximal end coupled to the receiving arm and having a track at a distal end of the clamping arm, and a sliding component including a needle and configured to slidably move along the track of the clamping arm.

In some embodiments, the clamping arm can have an indicator configured to represent a distance between at least a portion of the receiving arm and at least a portion of the clamping arm. In some embodiments, the receiving arm can have a coupling mechanism configured to be releasably coupled to an implant. In some embodiments, the needle of the sliding component can define a lumen therethrough, and the sliding component can define an opening in fluid communication with the lumen defined by the needle and configured to receive a fluid to be conveyed through the lumen.

In some embodiments, the track has a concave curvature with an inner surface of a concave portion facing toward the proximal end of the clamping arm. In some embodiments, the clamping arm can have a guide defining a lumen, and the needle can be configured to slidably move within the lumen when the sliding component is slidably moved along the track of the clamping arm.

In some embodiments, the track can be configured to rotatably move about an axis towards the receiving arm from a first position with respect to the receiving arm to a second position with respect to the receiving arm when the clamping arm is moved towards the receiving arm. The sliding component can be configured to slidably move along the track when the track is in the first position with respect to the receiving arm and configured to slidably move along the track when the track is in the second position with respect to the receiving arm.

In some embodiments, the needle is configured to slidably move through a lumen and configured to move into at least a portion of the receiving arm. In some embodiments, the receiving arm can be configured to be inserted into a body of a patient after the receiving arm is coupled to the at least the portion of the implant. In some embodiments, the clamping arm includes a side protrusion having a rough portion and a smooth portion.

In another general aspect, a medical device can include a receiving arm configured to receive at least a portion of an implant, a clamping arm coupled to the receiving arm and configured to move a track such that a distance between the track and the receiving arm is decreased, and a sliding component including a needle and configured to slidably move along the track such that the needle is moved toward the receiving arm.

In some embodiments, the track is a first track, at least one of the clamping arm or the receiving arm is configured slidably move along a second track such that the distance between the first track and the receiving arm is decreased. In some embodiments, the sliding component is configured to slidably move when the distance between the track and the receiving arm is decreased. In some embodiments, the medical device can include a locking mechanism configured to removably lock the clamping arm in a position with respect to the receiving arm after the distance between the track and the receiving arm has been decreased.

In some embodiments, the medical device can include an indicator mechanism configured to indicate a target position of the sliding component so that at least a portion of the needle is in contact with the implant when the sliding component is slidably moved along the track to the target position. In some embodiments, the medical device can include a safety stop configured to limit movement of the sliding component along the track.

In some embodiments, the needle coupled to the sliding component can have a coupling mechanism configured to be coupled to the implant after the sliding component has been moved toward the receiving arm. The clamping arm can be configured to move the track such that the distance between the track and the receiving arm is increased after the coupling mechanism of the needle has been coupled to the implant.

In some embodiments, the receiving arm is configured to be inserted into a vaginal region of a patient before the clamping arm is moved. The needle can be configured to pierce a skin tissue of the patient when the needle is moved toward the receiving arm. In some embodiments, the needle can be configured to pierce a tissue of a patient and to be coupled to the implant as the needle is moved toward the receiving arm. The sliding component can be configured to slidably move along the track away from the receiving arm such that the implant is pulled through the tissue of the patient after the needle has been coupled to implant.

In some embodiments, the track can have a curvature facing in the same direction as a curvature of a lumen of a guide of the clamping arm. The needle can be configured to slidably move within the lumen when the sliding component is slidably moved along the track of the clamping arm. In some embodiments, the sliding component can be configured to slidably move along the track of the clamping arm until at least a portion of the needle is disposed within the receiving arm.

In yet another general aspect, a method can include inserting at least a portion of a receiving arm of a medical device coupled to at least a portion of an implant into a body of a patient. The method can also include moving a sliding component along a track of a clamping arm such that a portion of a needle of the sliding component is moved into the body of the patient and is coupled to the portion of the implant.

In some embodiments, the method can include moving, before the moving of the sliding component, the clamping arm toward the receiving arm. In some embodiments, the moving can include moving the sliding component in a first direction. The method can include moving the sliding component coupled to the clamping arm in a second direction along the track of the clamping arm away from the receiving arm until the portion of the implant coupled to the portion of the needle of the sliding component is moved outside of the body of the patient.

In some embodiments, the moving can include moving the sliding component in a first direction. The method can include inserting the portion of the implant into a coupling mechanism of the receiving arm of the medical device before the inserting the portion of the receiving arm into the body of the patient. The portion of the implant can be coupled to a coupling mechanism of the portion of the needle portion in response to the moving of the sliding component. The method can include moving the sliding component coupled to the clamping arm in a second direction along the track of the clamping arm away from the receiving arm until the portion of the implant coupled to the portion of the needle of the sliding component is decoupled from the coupling mechanism of the receiving arm.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
a receiving arm configured to be coupled to at least a portion of an implant;
a clamping arm having a proximal end portion coupled to the receiving arm and having a track disposed at a distal end portion of the clamping arm; and
a sliding component including a needle, the sliding component configured to slidably move the needle along the track of the clamping arm,
the clamping arm rotatably coupled to the receiving arm, the clamping arm configured to rotate about an axis towards the receiving arm such that a distance between the track of the clamping arm and the receiving arm is decreased,
wherein the needle has a coupling mechanism configured to be coupled to the implant after the sliding component has been moved toward the receiving arm,
the track of the clamping arm configured to move such that the distance between the track and the receiving arm is increased after the coupling mechanism of the needle has been coupled to the implant.

2. The medical device of claim 1, wherein the clamping arm has an indicator configured to represent a distance between at least a portion of the receiving arm and at least a portion of the clamping arm.

3. The medical device of claim 1, wherein the receiving arm has a coupling mechanism configured to be releasably coupled to the implant.

4. The medical device of claim 1, wherein the needle defines a lumen therethrough, and the sliding component defines an opening that is in fluid communication with the lumen defined by the needle and configured to receive a fluid to be conveyed through the lumen.

5. The medical device of claim 1, wherein the track has a concave curvature with an inner surface of a concave portion facing toward the proximal end portion of the clamping arm.

6. The medical device of claim 1, wherein the clamping arm has a guide defining a lumen, the needle configured to slidably move within the lumen when the sliding component is slidably moved along the track of the clamping arm.

7. The medical device of claim 1, wherein the track is configured to rotatably move about the axis towards the receiving arm from a first position with respect to the receiving arm to a second position with respect to the receiving arm when the clamping arm is rotated towards the receiving arm,
the sliding component is configured to slidably move along the track when the track is in the first position with respect to the receiving arm and configured to slidably move along the track when the track is in the second position with respect to the receiving arm.

8. The medical device of claim 1, wherein the clamping arm has a proximal end portion and a distal end portion, the proximal end portion of the clamping arm rotatably coupled to the proximal end portion of the receiving arm via a hinge.

9. The medical device of claim 1, wherein the receiving arm is configured to be inserted into a body of a patient after the receiving arm is coupled to the at least the portion of the implant.

10. The medical device of claim 1, wherein the clamping arm includes a side protrusion having a rough portion and a smooth portion.

11. A medical device, comprising:
a receiving arm configured to receive at least a portion of an implant;
a clamping arm rotatably coupled to the receiving arm, the clamping arm defining a track, the track configured to rotate about an axis towards the receiving arm such that a distance between the track and the receiving arm is decreased; and
a sliding component including a needle, the sliding component configured to slidably move the needle along the track such that the needle is moved toward the receiving arm,
wherein the needle has a coupling mechanism configured to be coupled to the implant after the sliding component has been moved toward the receiving arm,
the clamping arm configured to move the track such that the distance between the track and the receiving arm is increased after the coupling mechanism of the needle has been coupled to the implant.

12. The medical device of claim 11, wherein the track is a first track, at least one of the clamping arm or the receiving arm is configured to slidably move along a second track such that the distance between the first track and the receiving arm is decreased.

13. The medical device of claim 11, wherein the sliding component is configured to slidably move when the distance between the track and the receiving arm is decreased.

14. The medical device of claim 11, further comprising:
a locking mechanism configured to removably lock the clamping arm in a position with respect to the receiving arm after the distance between the track and the receiving arm has been decreased.

15. The medical device of claim 11, further comprising:
an indicator mechanism configured to indicate a target position of the sliding component so that at least a portion of the needle is in contact with the implant when the sliding component is slidably moved along the track to the target position.

16. The medical device of claim 11, wherein the receiving arm is configured to be inserted into a vaginal region of a patient before the clamping arm is moved, the needle configured to pierce a skin tissue of the patient when the needle is moved toward the receiving arm.

17. The medical device of claim 11, wherein the needle is configured to pierce a tissue of a patient and to be coupled to the implant as the needle is moved toward the receiving arm,
the sliding component configured to slidably move along the track away from the receiving arm such that the implant is pulled through the tissue of the patient after the needle has been coupled to implant.

18. A method, comprising:
inserting at least a portion of a receiving arm of a medical device coupled to at least a portion of an implant into a body of a patient;
moving a clamping arm rotatably coupled to the receiving arm towards the receiving arm, the clamping arm having a track;
rotating the track about an axis towards the receiving arm when the clamping arm is moved towards the receiving arm;
moving a portion of a needle of a sliding component into the body of the patient by moving the sliding component coupled to the clamping arm in a first direction along the track of the clamping arm, the needle having a coupling mechanism that couples to the implant after the sliding component has been moved toward the receiving arm; and
increasing the distance between the track and the receiving arm by moving the track of the clamping arm and after the coupling mechanism of the needle has been coupled to the implant.

19. The method of claim 18, further comprising:
moving the sliding component in a second direction along the track away from the receiving arm until the portion of the implant coupled to the needle of the sliding component is moved outside of the body of the patient.

* * * * *